United States Patent
Biondo et al.

(10) Patent No.: US 10,964,919 B2
(45) Date of Patent: Mar. 30, 2021

(54) ORGANIC ELECTROLUMINESCENT TRANSISTOR

(71) Applicant: Flexterra, Inc., Skokie, IL (US)

(72) Inventors: Viviana Biondo, Illegio Tolmezzo (IT); Gianluca Generali, Bologna (IT); Andrea Stefani, Trento (IT); Michele Muccini, Bologna (IT); Guido Turatti, Bosco Mesola (IT); Mitchell Denti, Chicago, IL (US); Hakan Usta, Kayseri (TR); Xiaoyan Chen, Glenview, IL (US); Antonio Facchetti, Chicago, IL (US)

(73) Assignee: Flexterra Inc., Skokie, IL (US)

( * ) Notice: Subject to any disclaimer, the term of this patent is extended or adjusted under 35 U.S.C. 154(b) by 606 days.

(21) Appl. No.: 15/413,838

(22) Filed: Jan. 24, 2017

(65) Prior Publication Data
US 2017/0237042 A1    Aug. 17, 2017

Related U.S. Application Data

(63) Continuation of application No. PCT/US2015/042063, filed on Jul. 24, 2015.
(Continued)

(30) Foreign Application Priority Data

Jul. 24, 2014 (EP) .................................. 14425100
Jul. 24, 2014 (EP) .................................. 14425101

(51) Int. Cl.
*H01L 51/52* (2006.01)
*H01L 51/00* (2006.01)
(Continued)

(52) U.S. Cl.
CPC ...... *H01L 51/5296* (2013.01); *H01L 51/0074* (2013.01); *H01L 51/0085* (2013.01);
(Continued)

(58) Field of Classification Search
CPC ............. H01L 51/5296; H01L 51/0074; H01L 51/0085; H01L 51/0072; H01L 2251/303;
(Continued)

(56) References Cited

U.S. PATENT DOCUMENTS 9,825,261 B2 * 11/2017 Facchetti ............ H01L 51/0074
2006/0158397 A1 * 7/2006 Goh ..................... G09G 3/3233
345/76
(Continued)

FOREIGN PATENT DOCUMENTS

EP    2402348    1/2012
EP    2737559    6/2014
(Continued)

OTHER PUBLICATIONS

Jang et al, High Efficiency Green Phosphorescent Organic Light Emitting Device with (TCTA.TCTA0.5TPBi0.5/TPBi): Ir(ppy)3 Emission Layer, Thin Solid Films,vol. 517, Issue 14, pp. 4122-4126, (2009).*
(Continued)

*Primary Examiner* — Alexander C Kollias
(74) *Attorney, Agent, or Firm* — McDonnell Boehnen Hulbert & Berghoff LLP

(57) ABSTRACT

The present teachings relate to an organic electroluminescent transistor with improved light-emission characteristics. More specifically, the present organic electroluminescent transistor has an emissive ambipolar channel including at least one layer of an n-type semiconductor material, at least one layer of a p-type semiconductor material, and at least one layer of an emissive material arranged between the
(Continued)

layers of the p-type and n-type semiconductor materials, where the multilayer emissive ambipolar channel includes, among various layers, a layer of a p-type semiconductor material comprising a benzothieno-benzothiophene compound, and/or a layer of an emissive material comprising a blend material that includes an organic carbazole derivative as the host matrix compound and an iridium complex as the guest emitter.

20 Claims, 10 Drawing Sheets

Related U.S. Application Data

(60) Provisional application No. 62/028,397, filed on Jul. 24, 2014, provisional application No. 62/028,401, filed on Jul. 24, 2014.

(51) Int. Cl.
  *C07D 495/04* (2006.01)
  *H01L 51/05* (2006.01)
  *H01L 51/50* (2006.01)

(52) U.S. Cl.
  CPC ........ *C07D 495/04* (2013.01); *H01L 51/0061* (2013.01); *H01L 51/0072* (2013.01); *H01L 51/0562* (2013.01); *H01L 51/5012* (2013.01); *H01L 51/5016* (2013.01); *H01L 2251/301* (2013.01); *H01L 2251/303* (2013.01); *H01L 2251/305* (2013.01); *H01L 2251/308* (2013.01)

(58) Field of Classification Search
  CPC ........... H01L 2251/305; H01L 51/0061; H01L 2251/308; H01L 51/0562; H01L 51/5016; H01L 2251/301; H01L 51/5012; H01L 51/05; H01L 51/0508; H01L 51/102; H01L 2251/30; C07D 495/04
  See application file for complete search history.

(56) References Cited

U.S. PATENT DOCUMENTS

| | | | |
|---|---|---|---|
| 2008/0116815 A1* | 5/2008 | Foust | H01L 27/3204 315/185 R |
| 2010/0032655 A1* | 2/2010 | Takimiya | C07D 495/04 257/40 |
| 2010/0187512 A1* | 7/2010 | Ito | C07C 13/48 257/40 |
| 2010/0244000 A1 | 9/2010 | Tanaka et al. | |
| 2011/0024731 A1* | 2/2011 | Takimiya | C07C 391/02 257/40 |
| 2012/0286296 A1* | 11/2012 | So | B82Y 10/00 257/82 |
| 2012/0319093 A1* | 12/2012 | Muccini | H01L 51/5296 257/40 |
| 2015/0001518 A1 | 1/2015 | Capelli et al. | |

FOREIGN PATENT DOCUMENTS

| | | |
|---|---|---|
| JP | 2009152355 A | 7/2009 |
| JP | 2011258900 A | 12/2011 |
| WO | 2013017999 A1 | 2/2013 |
| WO | 2013/039842 | 3/2013 |
| WO | 2013128344 A1 | 9/2013 |
| WO | 2014/035842 | 3/2014 |

OTHER PUBLICATIONS

Myeong Jin Kang et al., "Two Isomeric Didecyl-dinaphtho [2,3-b : 2$'$,3$'$-f]thieno [3,2-b ]thiophenes: Impact of Alkylation Positions on Packing Structures and Organic Field Effect Transistor Characteristics", *Japanese Journal of Applied Physics*, 51: 11PD04, 2012.

Yu-Chang Chang et al., "Crystal Engineering for [pi]-[pi] Stacking via Interaction between Electron-Rich and Electron-Deficient Heteroaromatics", *J. Org. Chem.*, 73(12): 4608-4614, 2008.

Hideaki Ebata et al., "Highly Soluble(1)Benzothieno(3,2-b)benzothiophene(BTBT) Derivatives for High-Performance, Solution-Processed Organic Field-Effect Transistors", *JACS*, 129(51): 15732-15733, 2007.

Antonio Facchetti et al., "Synthesis and Characterization of Diperfluorooctyl-Substituted Phenylene-Thiophene Oligomers as n-Type Semiconductors. Molecular Structure-Film Microstructure-Mobility Relationships, Organic Field-Effect Transistors, and Transistor Nonvolatile Memory Elements" Chem. Mater., 16, 4715-4727 (2004).

* cited by examiner

ORGANIC ELECTROLUMINESCENT TRANSISTOR

CROSS-REFERENCE TO RELATED APPLICATIONS

This is a continuation of International Application No. PCT/US2015/042063 filed on Jul. 24, 2015, which claims priority to and the benefit of the filing dates of U.S. Provisional Patent Application Ser. No. 62/028,397 filed on Jul. 24, 2014, U.S. Provisional Patent Application Ser. No. 62/028,401 filed on Jul. 24, 2014, European Patent Application Serial No. 14425100.6 filed on Jul. 24, 2014, and European Patent Application Serial No. 14425101.4 filed on Jul. 24, 2014, the entire disclosure of each of which is incorporated by reference herein for all purposes.

FIELD

The present teachings relate to organic electroluminescent transistors with improved light emission characteristics. More specifically, the present electroluminescent transistors include a multilayer emissive ambipolar channel and by incorporating specific material(s) as one or more of the functional layers, the present electroluminescent transistors can achieve maximum brightness and efficiency simultaneously.

BACKGROUND

Organic electroluminescent field effect transistors, also known as OLETs (Organic Light Emitting Transistors) are a relatively recent type of devices, that have characteristics and applications that make them particularly interesting. For example, compared to OLEDs (Organic Light Emitting Diodes), ambipolar OLETs have enhanced efficiency and luminosity, and also can afford the possibility of using low-cost production processes once they have been optimized.

Further details about the structure of an ambipolar OLET device may be found in European Patent No. EP 1609195. More specifically, EP 1609195 discloses a three-layer organic light emitting transistor having an emissive ambipolar channel that includes at least one layer of an n-type semiconductor material, at least one layer of a p-type semiconductor material and at least one layer of an emissive material arranged between said layers of p-type and n-type semiconductor materials. Further details about the applications and the functional characteristics of these devices may be found in R. Capelli et al., "Organic light-emitting transistors with an efficiency that outperforms the equivalent light-emitting diodes," *Nature Materials*, vol. 9, pp. 496-503 (2010). The three-layer organic light-emitting transistor disclosed in Capelli et al. has a layer of an n-type semiconductor material composed of 5,5'-bis((5-perfluorohexyl) thiophen-2-yl)-2,2'-bithiophene (DFH4T), a layer of a p-type semiconductor material composed of 5,5'-bis(3-hexyl-2-thienyl)-2,2'-bithiophene (DH4T), and a layer of an emissive material composed of tris(8-hydroxyquinolinato) aluminium:4-(dicyanomethylene)-2-methyl-6-(p-dimethylaminostyryl)-4H-pyran ($Alq_3$:DCM).

Among different p-type semiconductor materials that have been reported in the literature, diacene-fused thienothiophenes, specifically, [1]benzo-thieno[3,2-b][1]benzothiophenes (BTBTs) and dinaphtho[2,3-b:2',3'-f]thieno[3,2-b] thiophenes (DNTTs) have been shown to exhibit high mobility, air stability, and good reproducibility. See e.g., M.

J. Kang et al., "Two Isomeric Didecyl-dinaphtho[2,3-b:2', 3'-f]thieno[3,2-b]thiophenes: Impact of Alkylation Positions on Packing Structures and Organic Field Effect Transistor Characteristics," *Jpn. J. Appl. Phys.*, vol. 51, pp. 11PD04 (2012); and H. Ebata et al., "Highly Soluble [1]Benzothieno [3,2-b]benzothiophene (BTBT) Derivatives for High-Performance, Solution-Processed Organic Field-Effect Transistors," *J. Am. Chem. Soc.*, vol. 129, pp. 15732-15733 (2007). In Ebata et al., a series of 2,7-dialkylderivatives of BTBT ($C_n$-BTBT) were synthesized and used to fabricate organic field-effect transistors (OFETs). The OFETs were evaluated under ambient conditions and thin films of $C_n$-BTBT derivatives were shown to provide mobilities higher than $10^{-1}$ cm$^2$ V$^{-1}$ s$^{-1}$. In Kang et al., two isomeric dodecyl-dinaphtho[2, 3-b:2',3'-f]thieno[3,2-b]thiophenes (2,9- and 3,10-$C_{10}$ DNTTs) were shown to afford high-performance OFETs with an average mobility of 6.8 cm$^2$ V$^{-1}$ s$^{-1}$ for 2,9-$C_{10}$-DNTT, and an average mobility of 4 cm$^2$ V$^{-1}$ s$^{-1}$ for 3,10-$C_{10}$-DNTT.

European Patent Application Publication No. EP 2402348 describes dialkyl-substituted DNTTs and related selenium analogs. OTFTs fabricated with the described compounds showed mobilities close to 4 cm$^2$ V$^{-1}$ s$^{-1}$. No BTBT compounds are described.

International Publication Number WO 2013/039842 describes various acene-fused thienothiophenes and related chalcogen analogs that are mono- or bis-substituted with branched alkyl. OTFTs fabricated with the described compounds showed mobilities close to 2.3 cm$^2$ V$^{-1}$ s$^{-1}$. No BTBT compounds are described.

Each of the above-identified documents is silent as to the possibility of using BTBT compounds in an OLET device having a trilayer emissive ambipolar channel and how the performance of such OLET device may compare to a similar OLET device using DNTT compounds.

So far, all studies and characterizations have shown that ambipolar OLET devices have an enhanced luminosity, though obtained at bias conditions where the efficiency of charge current conversion into light emission is very low (in the order of 1×10$^{-1}$%). Conversely, the device efficiency can be usually maximized by modifying its bias conditions but with detrimental effects on the luminosity. These emission characteristics limit the possible application fields when high brightness and high efficiency are simultaneously needed such as, for example, in the fields of light emitting displays, Point of Care biomedical applications, and photon sources integrated on photonic chips. Further improvements in electroluminescence intensity (from the order of nanoWatt (nW) to microWatt (µV) with constant device geometry) also is desirable.

SUMMARY

An objective of the present teachings is to provide an organic electroluminescent transistor that can overcome the above mentioned drawbacks known in the art, in particular, to provide an organic electroluminescent transistor that can achieve maximum light emission efficiency and brightness simultaneously.

In one aspect, an organic electroluminescent transistor according to the present teachings comprises at least one dielectric layer, at least one control electrode, an assembly comprising an emissive ambipolar channel, at least one source electrode and at least one drain electrode, wherein:

the dielectric layer is arranged between the control electrode and the assembly;

the ambipolar channel comprises at least one layer of an n-type semiconductor material, at least one layer of a p-type semiconductor material and at least one layer of an emissive material arranged between the layers of p-type and n-type semiconductor materials; and the p-type semiconductor material is suitable to transport holes across the ambipolar channel of the transistor and comprises a benzothieno-benzothiophene (BTBT) compound having general formula (P-I)

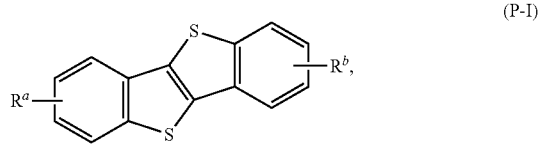

(P-I)

wherein $R^a$ and $R^b$ are independently selected from the group consisting of H, a $C_{1-18}$ alkyl group, and a $C_{6-14}$ aryl group.

In certain embodiments, the n-type semiconductor material is a bis(p-fluoroalkyl)phenyl-substituted thieno[3,2-b]thiophene, non-limiting examples of which include 2,5-bis(4-(perfluorooctyl)phenyl)thieno[3,2-b]thiophene (NF2-6) and 2,5-bis(4-(trifluoromethyl)phenyl)thieno[3,2-b]thiophene (NF2-6-CF3).

In certain embodiments, the emissive layer is selected from the group consisting of 4,4',4''-tris(carbazole-9-yl)triphenylamine:tris(1-phenylisoquinoline) iridium(III) (TCTA:Ir(piq)$_3$), 4,4'-bis(3,6-dineopentyl-9H-carbazole-9-yl)-1,'-biphenyl:tris(1-phenylisoquinoline)iridium(III) (NP4-CBP:Ir(piq)$_3$), 4,4'-bis(3,6-dineopentyl-9H-carbazole-9-yl)-1,'-biphenyl:tris(2-phenylpyridine)iridium(III) (NP4-CBP:Ir(ppy)), 4,4'-bis(3,6-dineopentyl-9H-carbazole-9-yl)-1,'-biphenyl:bis(4,6-difluorophenyl-pyridine)(picolinate)iridium(III) (NP4-CBP:FIrpic).

In another aspect, an organic electroluminescent transistor according to the present teachings comprises at least one dielectric layer, at least one control electrode, an assembly comprising an emissive ambipolar channel, at least one source electrode and at least one drain electrode, wherein:

the dielectric layer is arranged between the control electrode and the assembly;

the ambipolar channel comprises at least one layer of an n-type semiconductor material, at least one layer of a p-type semiconductor material and at least one emissive layer of an emissive material arranged between the layers of the p-type and n-type semiconductor materials; and wherein the emissive layer comprises a blend material comprising a carbazole derivative as a host matrix compound and an iridium complex as a guest emitter.

In various embodiments, the organic electroluminescent transistor can include one or more additional layers selected from the group consisting of a hole-injection sublayer, an electron-injection sublayer, and a passivation layer. In one embodiment, as example, the source electrode is in contact with the layer of p-type semiconductor material and the drain electrode is in contact with the layer of n-type semiconductor material. In another embodiment, an injection sublayer can be interposed between the source electrode and the layer of p-type or n-type semiconductor material and/or an injection sublayer is interposed between the drain electrode and the layer of p-type or n-type semiconductor material.

The foregoing as well as other features and advantages of the present teachings will be more clearly understood from the following figures, description, examples, and claims. The claims as filed are an integral part of this specification and are herein incorporated by reference.

DETAILED DESCRIPTION

Figure 1:
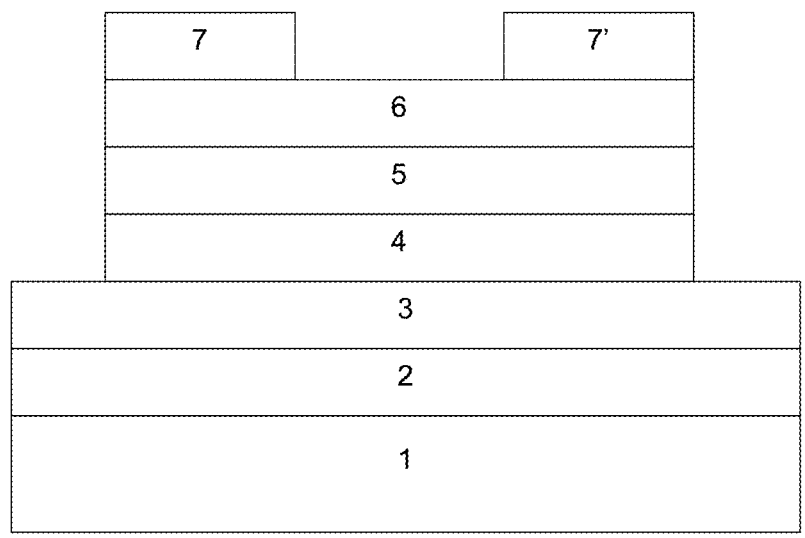
FIG. 1 is a cross-sectional view of an organic light emitting transistor (OLET) according to an embodiment of the present teachings, which includes a substrate (1), a control electrode (2), a dielectric layer (3), an assembly comprising an emissive ambipolar channel that includes a layer of a first-type of semiconductor material (4), a layer of an emissive material (5), a layer of a second-type of semiconductor material (6), and an electron electrode and a hole electrode (7 and 7').

FIG. 1 shows the structure of an organic electroluminescent transistor (OLET) according to an embodiment of the present teachings. In this particular embodiment, the OLET includes a substrate 1 that acts as a supporting layer, over which there is an electrode 2 that acts as the control (or gate) electrode and that may be a transparent electrode, and a layer of dielectric material 3, over which there is a light-emitting assembly. The light-emitting assembly generally includes a charge carrier transport layer of a first type 4, a layer 5 of emissive material, and a charge carrier transport layer of a second type 6. The charge carrier transport layer of the first type 4, for example, can be a hole transport layer made of a p-type semiconductor material and the charge carrier transport layer of the second type 6 can be an electron transport layer made of an n-type semiconductor material, although an inverted assembly (with layer 4 being an electron transport layer made of an n-type semiconductor material and layer 6 being a hole transport layer made of a p-type semiconductor material) also can be used. Hole and electron electrodes 7 and 7' are realized so as to inject charge carriers into the light-emitting assembly. In the shown embodiment, the hole and electron electrodes are directly in contact with the charge carrier transport layer of the second type 6. According to certain embodiments (not shown), an injection sublayer (i.e., a hole-injection sublayer) can be interposed between the hole electrode and the layer 6 in embodiments where the layer 6 is a layer of p-type semiconductor material. In embodiments where the layer 6 is a layer of n-type semiconductor material, an injection sublayer (i.e., an electron-injection sublayer) can be interposed between the electron electrode and the layer 6.

As understood by those skilled in the art, the hole electrode and the electron electrode can function, respectively, as the source electrode and the drain electrode (or vice versa) depending on the polarity of the gate voltage. Briefly, because the source electrode is typically grounded (0 V), if the gate voltage is −100V and the drain voltage is −80V, then the source electrode is the hole electrode (negatively biased) and the drain electrode is the electron electrode (positively biased). On the other hand, if the gate voltage is +100V, the source electrode is the electron electrode and the drain electrode is the hole electrode. An OLET typically is operated by applying a first appropriate bias voltage to the gate electrode, and injecting electrons from the electron electrode and holes from the hole electrode, while maintaining a second bias voltage between the latter two electrodes. In some embodiments, the first and second bias voltages can be continuous voltages. In other embodiments, the first and second bias voltages can be pulsed voltages.

Instead of the bottom-gate architecture depicted in FIG. 1, an OLET can have a top-gate architecture. Further, the hole and electron electrodes and/or the control electrode can have alternative arrangements as described in International Publication No. WO 2014/035841. Specifically, the hole and electron electrodes can be in contact with different layers of the light-emitting assembly. For example, the hole electrode can be in contact with the layer of p-type semiconductor material, while the electron electrode can be in contact with the layer of n-type semiconductor material. Furthermore, as described in International Publication Nos. WO 2013/018002, WO 2013/017999, WO 2014/035842, and WO 2013/018000, additional control electrode(s) and/or additional layer(s) of dielectric material, emissive material, and/or charge carrier transport materials can be incorporated into the OLET. Optionally, a passivation layer can be present covering the top surface of the emissive ambipolar channel.

The inventors have found that the foregoing organic electroluminescent transistors such as, but not limited to, those configured according to the embodiment shown in FIG. 1, can have enhanced light emission if the p-type semiconductor material includes a benzothieno-benzothiophene (BTBT) compound of the formula (P-I):

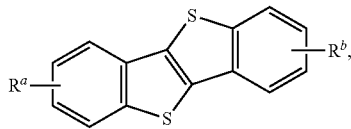

(P-I)

where $R^a$ and $R^b$ are independently selected from the group consisting of H, a $C_{1-18}$ alkyl group, and a $C_{6-14}$ aryl group. In preferred embodiments, the benzothieno-benzothiophene compound can have the formula:

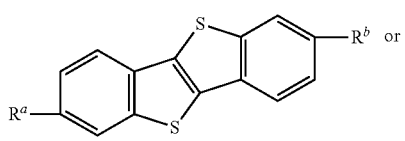

or

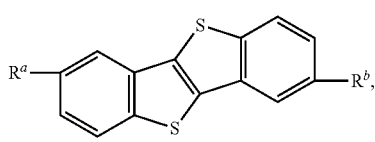

wherein $R^a$ and $R^b$ are identical $C_{1-18}$ alkyl groups, preferably identical $C_{3-12}$ alkyl groups, and most preferably identical linear $C_{3-12}$ alkyl groups. Specific non-limiting examples include 2,7-dioctyl[1]benzo-thieno[3,2-b][1] benzothiophene (C8-BTBT) and 2,7-dipentyl[1]benzo-thieno[3,2-b][1] benzothiophene (C5-BTBT).

In an alternative embodiment, the benzothieno-benzothiophene compound can have the formula:

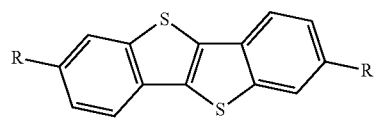

wherein each R can be a phenyl group.

The inventors surprisingly have found that although various p-type organic semiconducting compounds are known in the art (such as 5,5'-bis(3-hexyl-2-thienyl)-2,2'-bithiophene (DH4T) reported in R. Capelli et al., "Organic light-emitting transistors with an efficiency that outperforms the equivalent light-emitting diodes," *Nature Materials*, vol. 9, pp. 496-503 (2010)), the use of BTBT compounds as the p-type semiconductor material in an OLET device having a trilayer emissive ambipolar channel can lead to the simultaneous achievement of high electroluminescence and efficiency. Meanwhile, in previously reported devices, the use of other p-type semiconductor material such as DH4T inevitably could only either optimize electroluminescence at the expense of low efficiency or optimize efficiency at the expense of low electroluminescence but could not optimize both electroluminescence and efficiency under the same operating conditions as shown in the Examples below.

The inventors also unexpectedly found that, although dinaphtho[2,3-b:2',3'-f]thieno[3,2-b]thiophenes (DNTTs) are often considered very similar to BTBT compounds given their structural similarities and comparable hole mobilities as having been reported in the literature, OLET devices incorporating a DNTT compound as the p-type semiconductor material in the trilayer emissive ambipolar channel have significantly lower electroluminescence compared to OLET devices according to the present teachings.

Further enhanced emissive properties also may be obtained if the emissive material comprises a blend of an organic carbazole-based host matrix compound and an iridium complex guest emitter. More specifically, the organic carbazole-based host matrix compound can be represented by either formula (H-1) (TCTA), formula (H-2) (NP4-CBP), or formula (H-3) (CBP or 4,4'-bis(N-carbazolyl)-1,1'-biphenyl) and a guest emitter represented by formula (G-1) (FIrpic), formula (G-2) (Ir(ppy)), or formula (G-3) (Ir(piq)₃) as provided below. In various embodiments, the layer of emissive material can include between 5% and 22% of its total weight of the guest emitter.

For example, in embodiments where the emissive material is blue-emitting, the emissive material can include a blend of the arylamine matrix compound of (H-1) and the blue emitter of formula (G-1):

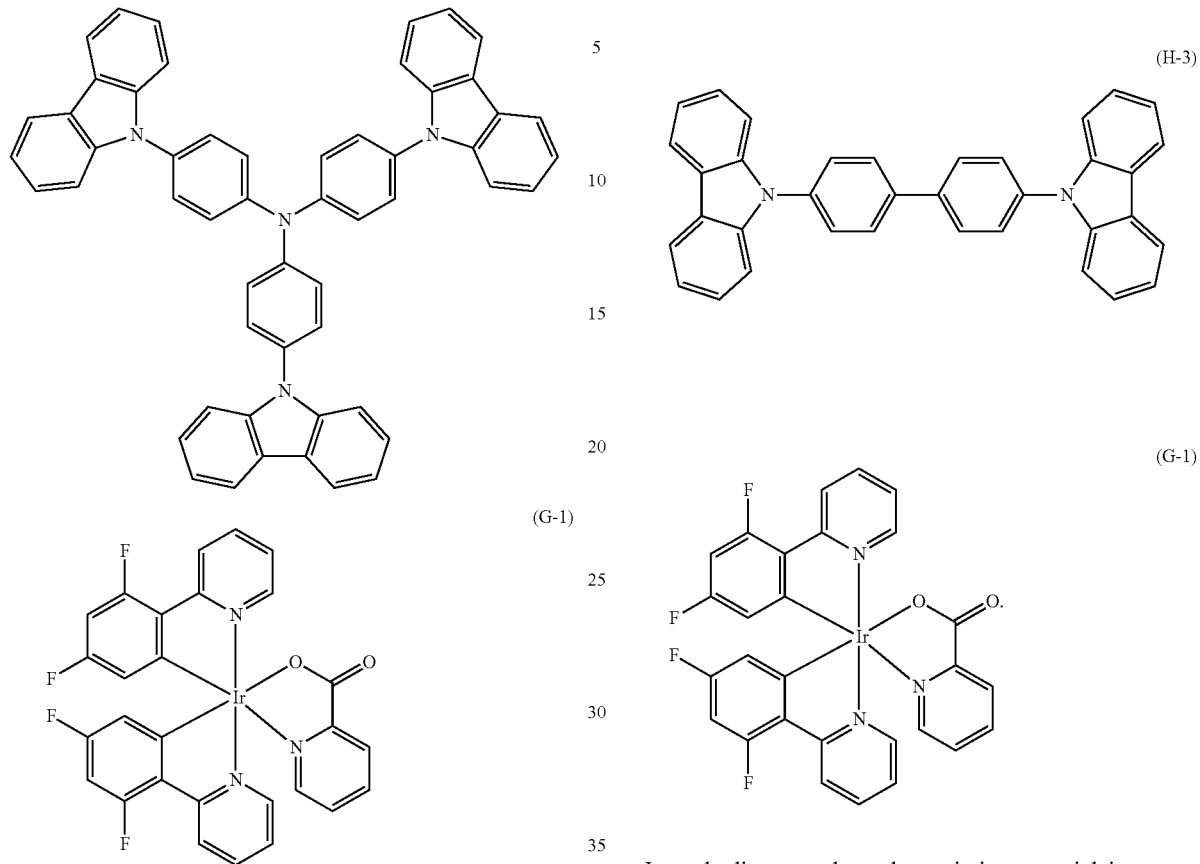
or a blend of the arylamine matrix compound of formula (H-2) and the blue emitter of formula (G-1):
or a blend of the arylamine matrix compound of formula (H-3) and the blue emitter of formula (G-1):
In embodiments where the emissive material is green-emitting, the emissive material can include a blend of the arylamine matrix compound of formula (H-1) and the green emitter of formula (G-2):
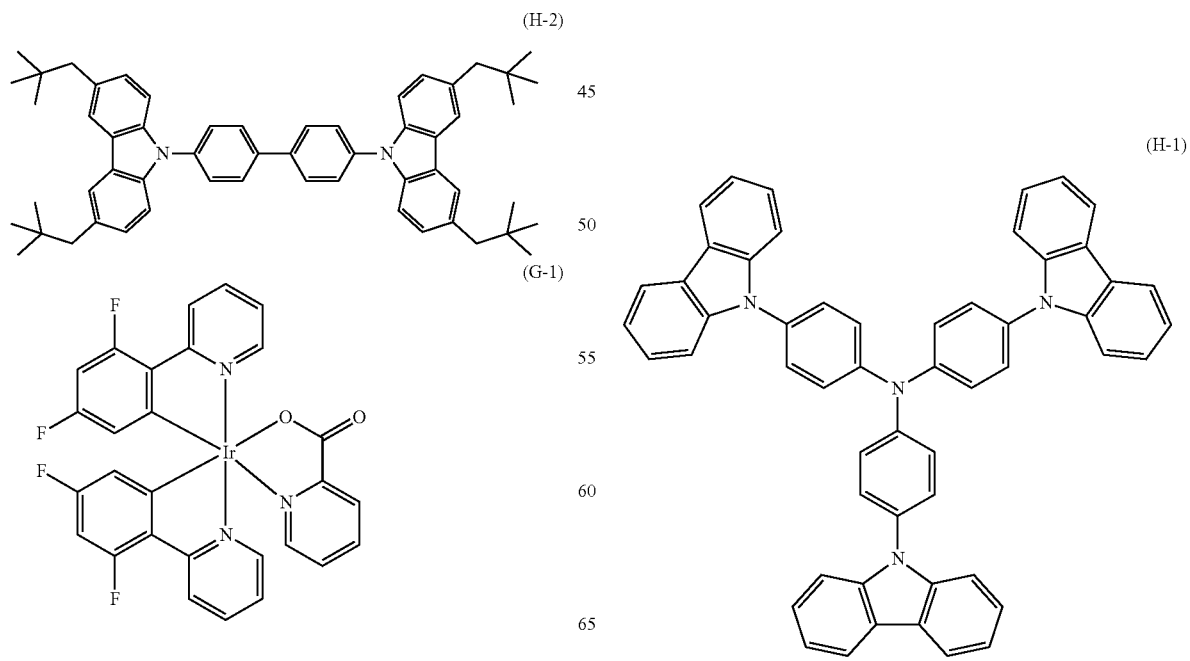

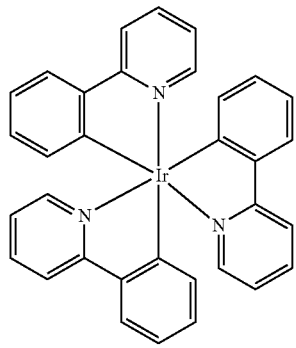
(G-2)

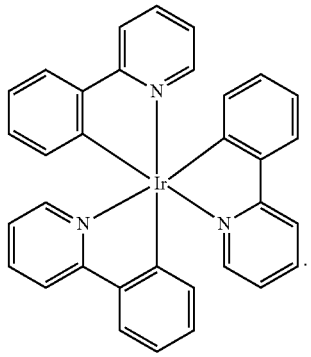
(G-2)

or a blend of the arylamine matrix compound of formula (H-2) and the green emitter of formula (G-2):

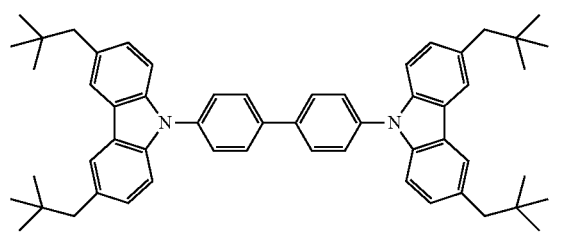
(H-2)

In embodiments where the emissive material is red-emitting, the emissive material can include a blend of the arylamine matrix compound of formula (H-1) and the red emitter of formula (G-3):

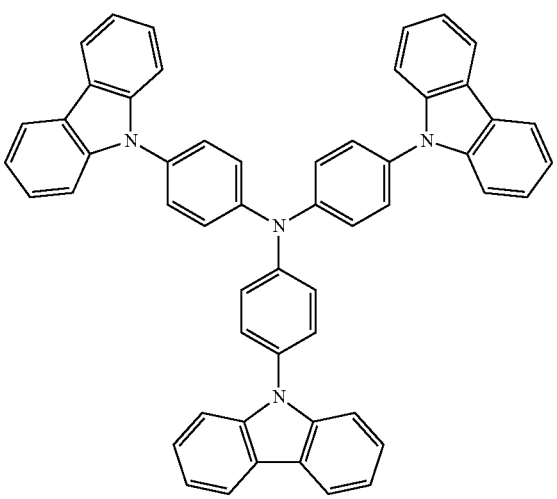
(H-1)

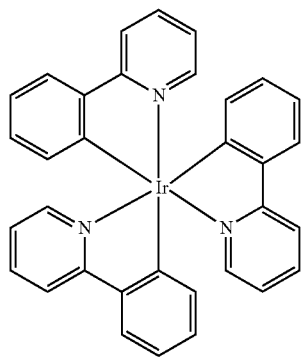
(G-2)

or a blend of the arylamine matrix compound of formula (H-3) and the green emitter of formula (G-2):

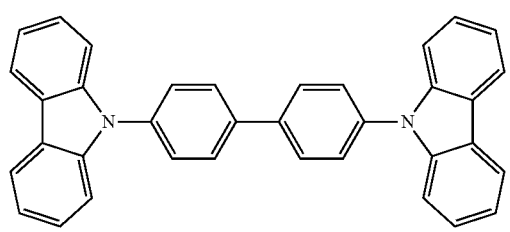
(H-3)

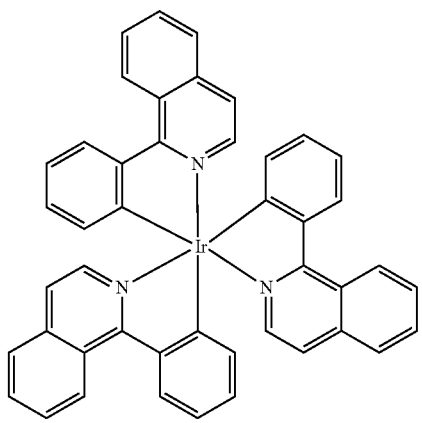
(G-3)

or a blend of the arylamine matrix compound of formula (H-2) and the red emitter of formula (G-3):

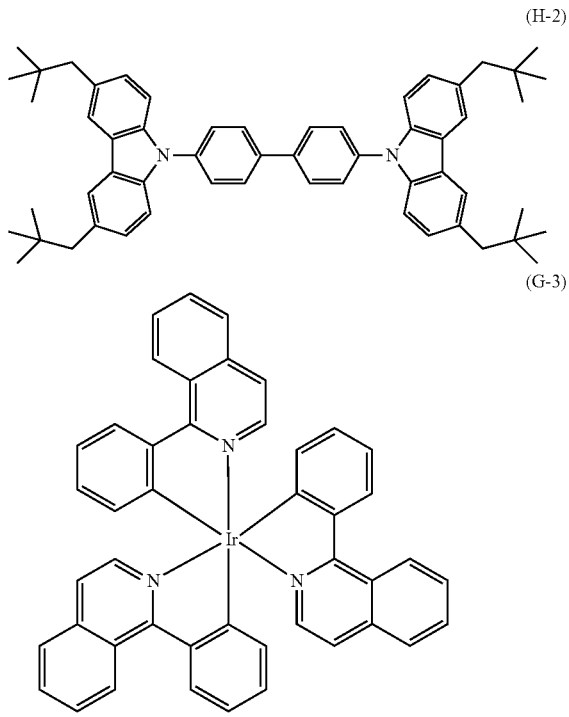

(H-2)

(G-3)

or a blend of the arylamine matrix compound of formula (H-3) and the red emitter of formula (G-3):

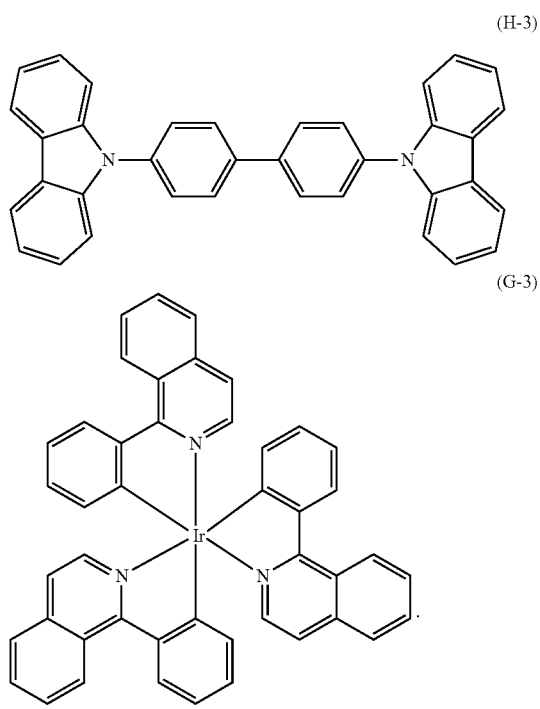

(H-3)

(G-3)

However, the emissive material can be selected from various single-component host-emitting materials and blend materials including a host matrix compound and a guest fluorescent or phosphorescent emitter known in the art. Suitable organic electroluminescent light-emitting materials include those having been used in OLED applications. For example, an alternative emissive material can be a blend of tris(8-hydroxyquinolinato)aluminium ($Alq_3$) as the host matrix compound and 4-(dicyanomethylene)-2-methyl-6-(p-dimethylaminostyryl)-4H-pyran (DCM) as the guest emitter.

Various examples of host materials, guest emitters, and single-component host-emitting materials are described in Chaskar et al., "Bipolar Host Materials: A Chemical Approach for Highly Efficient Electrophosphorescent Devices," *Adv. Mater.*, 23(34): 3876-3895 (2011); Tao et al., "Organic host materials for phosphorescent organic light-emitting diodes," *Chem. Soc. Rev.*, 40(5): 2943-2970 (2011); Sasabe et al., "Multifunctional Materials in High-Performance OLEDs: Challenges for Solid-State Lighting," *Chem. Mater.*, 23(3): 621-630 (2011); Tsuboi, "Recent advances in white organic light emitting diodes with a single emissive dopant," *J. Non-Cryst. Solids*, 356(37-40): 1919-1927 (201); Singh et al., "Bio-organic optoelectronic devices using DNA," *Adv. Polym. Sci.*, 223 (Organic Electronics): 189-212 (2010); Kappaun et al., "Phosphorescent organic light-emitting devices: working principle and iridium based emitter materials," *Int. J. Mol. Sci.*, 9(8): 1527-1547 (2008); Tokito et al., "Phosphorescent organic light-emitting devices: triplet energy management," *Electrochemistry*, 76(1): 24-31 (2008); Chen, "Evolution of Red Organic Light-Emitting Diodes: Materials and Devices," *Chem. Mater.*, 16(23): 4389-4400 (2004); Liu et al., "Polyfluorenes with on-chain metal centers," *Adv. Poly. Sci.*, 212 (Polyfluorenes): 125-144 (2008); Danev et al., "Vacuum deposited polyimide—a perfect matrix for nanocomposite materials," *J. Optoelectron. Adv. Mater.*, 7(3): 1179-1190 (2005); U.S. Pat. Nos. 5,747,183; 5,683,823; 6,626,722; 7,074,502; 7,671,241; and 7,772,762.

To illustrate, some exemplary host-emitting materials include phosphorescent host-emitting compounds based on carbazole derivatives, fluorene derivatives, or 9-naphthylanthracene derivatives, and fluorescent host-emitting compounds based on organometallic chelates such as tris(8-quinolinol)aluminum complexes. Some exemplary host materials include polymers such as poly(p-phenylene vinylene), poly(alkyphenylphenylvinylene), poly(alkyphenylphenylvinylene-co-alkoxyphenylenevinylene), polyfluorene, poly(n-vinylcarbazole), and copolymers thereof. Various carbazole compounds, triphenylamine compounds, including hybrids with oxadiazole or benzimidazole also have been used as host materials.

Some exemplary guest emitters (light-emitting dyes or dopants) include fluorescent dyes such as various perylene derivatives, anthracene derivatives, rubrene derivatives, carbazole derivatives, fluorene derivatives, and quinacridone derivatives, and phosphorescent emitters such as various transition metal complexes including Ir, Os, or Pt. Tests carried out by the applicant showed that light emission figures are further enhanced when the emissive layer is selected among TCTA:$Ir(piq)_3$, NP4-CBP:$Ir(piq)_3$, NP4-CBP:Ir(ppy), NP4-CBP:FIrpic. According to one embodiment, the layer of emissive material contains a concentration of a doping material (e.g. one of the above described transition metal complexes) that is comprised between 5 and 22% of the total weight of the emissive layer.

In certain embodiments, the n-type semiconductor material can include a bis(p-fluoroalkyl)phenyl-substituted oligomeric thiophene compound, where the oligomeric thiophene compound can have 2, 3, 4, 5 or 6 thiophene moieties, optionally where two or more of the thiophene moieties can be fused. For example, the bis(p-fluoroalkyl)phenyl-substituted oligomeric thiophene compound can be selected from the group consisting of a dithiophene, a quaterthiophene, and a thienothiophene, The inventors have found that the foregoing organic electroluminescent transistors can have enhanced emissive properties if the n-type semiconductor material includes an electron-transporting compound represented by formula (N-1):

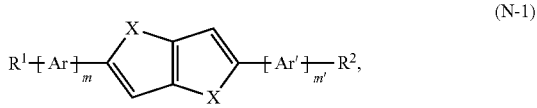

(N-1)

wherein:

X is selected from the group consisting of S, O, and Se;

Ar and Ar', at each occurrence, independently are identical or different monocyclic aryl or heteroaryl groups;

$R^1$ and $R^2$ independently are identical or different electron-withdrawing groups selected from the group consisting of —CN, $R^3$, —C(O)$R^4$, and —C(O)O$R^4$; wherein $R^3$ is an alkyl, alkenyl, or alkynyl group substituted with one or more F or CN groups, and $R^4$ is an alkyl, alkenyl, or alkynyl group optionally substituted with one or more F or CN groups; and m and m' independently are 1 or 2.

For example, $R^1$ and $R^2$ can be $R^3$ which is selected from the group consisting of (i) a $C_{1-20}$ alkyl group substituted with one or more F or CN groups having the general formula $C_xF_yH_{2x+1-y}$ or $C_xCN_yH_{2x+1-y}$, provided that x is an integer ranging between 1 and 20, y is an integer ranging between 1 and 41, and $y \leq 2x+1$; (ii) a $C_{2-20}$ alkenyl group substituted with one or more F or CN groups having the general formula $C_xF_yH_{2x-1-y}$ or $C_xCN_yH_{2x-1-y}$, provided that x is an integer ranging between 2 and 20, y is an integer ranging between 1 and 39, and $y \leq 2x-1$; (iii) a $C_{2-20}$ alkynyl group substituted with one or more F or CN groups having the general formula $C_xF_yH_{2x-3-y}$ or $C_xCN_yH_{2x-3-y}$, provided that x is an integer ranging between 2 and 20, y is an integer ranging between 1 and 37, and $y \leq 2x-3$. In certain embodiments, $R^1$ and $R^2$ can be a $C_{1-20}$ alkyl group substituted with one or more F groups having the general formula $C_xF_yH_{2x+1-y}$, provided that x is an integer ranging between 1 and 20, y is an integer ranging between 1 and 41, and $y \leq 2x+1$. In particular embodiments, $R^1$ and $R^2$ can be a $C_{1-18}$ perfluoroalkyl group having the general formula $C_nF_{2n+1}$, provided that n is an integer ranging between 1 and 20.

In other embodiments, $R^1$ and $R^2$ can be —C(O)$R^4$ or —C(O)O$R^4$, where $R^4$ is selected from the group consisting of (i) H, (ii) a $C_{1-18}$ alkyl group optionally substituted with one or more F or CN groups having the general formula $C_xF_yH_{2x+1-y}$ or $C_xCN_yH_{2x+1-y}$, provided that x is an integer ranging between 1 and 20, y is an integer ranging between 0 and 41, and $y \leq 2x+1$ (ii) a $C_{2-18}$ alkenyl group optionally substituted with one or more F or CN groups having the general formula $C_xF_yH_{2x-1-y}$ or $C_xCN_yH_{2x-1-y}$, provided that x is an integer ranging between 2 and 20, y is an integer ranging between 0 and 39, and $y \leq 2x-1$; and (iii) a $C_{2-18}$ alkynyl group substituted with one or more F or CN groups having the general formula $C_xF_yH_{2x-3-y}$ or $C_xCN_yH_{2x-3-y}$, provided that x is an integer ranging between 2 and 20, y is an integer ranging between 0 and 37, and $y \leq 2x-3$.

In preferred embodiments, the electron-transporting compound can be represented by formula (N-2):

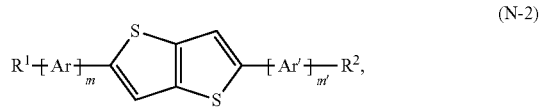

(N-2)

wherein Ar, Ar', $R^1$, $R^2$, m and m' are as defined herein.

In more preferred embodiments, the electron-transporting compound can be represented by formula (N-3):

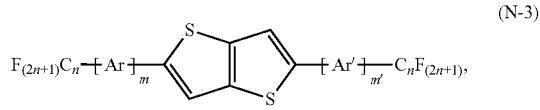

(N-3)

wherein n is an integer ranging from 1 to 12 (inclusive), preferably, from 4 to 12 (inclusive), and wherein Ar, Ar', m and m' are as defined herein.

In any of the foregoing embodiments, Ar and Ar', at each occurrence, independently can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group.

In particular embodiments, the electron-transporting compound can be represented by formula (N-4):

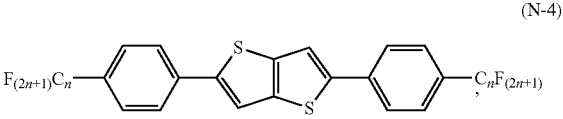

(N-4)

wherein n is an integer ranging from 1 to 12 (inclusive), and preferably, from 4 to 12 (inclusive).

In one specific embodiment, the electron-transporting compound can be 2,5-bis(4-(perfluorooctyl)phenyl)thieno[3,2-b]thiophene (N-F2-6):

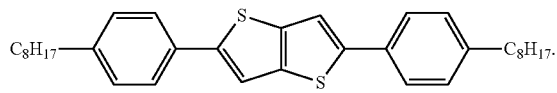

In another specific embodiment, the electron-transporting compound can be 2,5-bis(4-(trifluoromethyl)phenyl)thieno[3,2-b]thiophene (NF2-6-CF3):

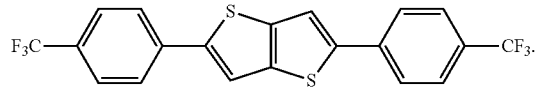

The dielectric layer can be an electrically insulating material selected from the group consisting of an inorganic oxide or nitride, a molecular dielectric, a polymeric dielectric, and combination thereof. In embodiments where the dielectric layer is a metal oxide or nitride, such dielectric material can be selected from the group consisting of $SiO_2$, $Si_3N_4$, $Al_2O_3$, $ZrO_x$, Al-doped $ZrO_x$, and $HfO_x$. In embodiments where the dielectric layer is a molecular dielectric, such dielectric can be a self-assembled nanodielectric. In embodiments where the dielectric layer is a polymeric dielectric, such dielectric material can be selected from the group consisting of polyolefins, polyacrylates, polyimides, polyesters, and fluoropolymers. Hybrid organic/inorganic materials also may be used. In preferred embodiments, the dielectric layer comprises an organic dielectric, particularly, a polymeric dielectric.

Another aspect of the present teachings is directed to organic electroluminescent transistors including at least one dielectric layer, at least one control electrode, an assembly comprising an emissive ambipolar channel, at least one source electrode and at least one drain electrode, wherein:

the dielectric layer is arranged between the control electrode and the assembly;

the ambipolar channel comprises at least one layer of an n-type semiconductor material, at least one layer of a p-type semiconductor material and at least one emissive layer of an emissive material arranged between the layers of the p-type and n-type semiconductor materials; and wherein the emissive layer is composed of a blend material that includes an organic carbazole derivative as the host matrix compound and an iridium complex as the guest emitter.

For example, as described above, the organic carbazole-based host matrix compound can be represented by either formula (H-1) (TCTA), formula (H-2) (NP4-CBP), or formula (H-3) (CBP or 4,4'-bis(N-carbazolyl)-1,1'-biphenyl) and the guest emitter can be represented by formula (G-1) (FIrpic), formula (G-2) (Ir(ppy)), or formula (G-3) (Ir $(piq)_3$).

The inventors surprisingly have found that although various host-guest emitter systems are known in the art, the use of a blend material that includes an organic carbazole-based host matrix compound and an iridium complex guest emitter as the emissive material in an OLET device having a trilayer emissive ambipolar channel can lead to the simultaneous achievement of high electroluminescence and efficiency. Meanwhile, in previously reported devices, the use of a metal complex host matrix compound (such as $Alq_3$) in combination with a metal complex guest emitter that is not iridium-based inevitably could only either optimize electroluminescence at the expense of low efficiency or optimize efficiency at the expense of low electroluminescence but not both electroluminescence and efficiency under the same operating conditions as shown in the Examples below.

OLETs according to the present teachings can be fabricated using processes known in the art. For example, organic layers (e.g., the layer of emissive material, the layers of p-type and n-type semiconductor materials, and the organic dielectric layer of certain embodiments) can be formed by vapor-phase processes such as chemical vapor deposition or physical vapor deposition, as well as solution-phase processes such as printing (e.g., flexo printing, litho printing, gravure printing, ink-jetting, pad printing, and so forth), drop casting, slot coating, dip coating, doctor blading, roll coating, or spin-coating.

The hole/electron and gate electrodes can be formed using conventional processing techniques. For example, any of the electrical contacts can be deposited through a mask, or can be deposited then etched or lifted off (photolithography). Suitable deposition techniques include electrodeposition, vaporization, sputtering, electroplating, coating, laser ablation and offset printing, from the same or different metals or metal alloys such as copper, aluminum, gold, silver, molybdenum, platinum, palladium, copper, titanium, chromium, and/or nickel, a transparent conducting oxide such as tin-doped indium oxide (ITO), or an electrically conductive polymer such as polyethylenethioxythiophene (PEDOT). Charge carrier injection can be facilitated by the use of a material for the injection electrode (hole electrode or electron electrode) that has a low barrier against injection of a charge carrier type into the hole transport sublayer and the electron transport sublayer, respectively. For example, the electron electrode can comprise one or more elements selected from the group consisting of Au, Ca, Mg, Al, In, and a perovskite manganites ($RE_{1-x}A_xMnO_3$, RE=rare earth element such as La, Nd, Pr etc., A=alkaline metal). The hole electrode can comprise at least one material selected from the group consisting of Au, indium tin oxide, Cr, Cu, Fe, Ag, poly(3,4-ethylenedioxthiophene) combined with poly(styrenesulfonate) (PEDOT:PSS), and a perovskite manganite ($Re_{1-x}A_xMnO_3$). In certain embodiments, the hole electrode and the electron electrode can be made of conductors with different work functions to favor both hole and electron injection.

If present, the hole and electron injection sublayers can be prepared by self-assembly of thiolates, phosphonates, or aliphatic or aromatic carboxylates; by thermal evaporation of various charge transfer complexes and other heteroaromatic or organometallic complexes; or by thermal evaporation or sputtering of various metal oxides, fluorides, or carbonates. The hole injection sublayer and the electron injection sublayer can be made of materials that provide a staircase of electronic levels between the energy level of the hole electrode and the electron electrode, and the energy level required for injection into the hole transport sublayer and the electron transport sublayer, respectively. See e.g., Li et al., "Low operating-voltage and high power-efficiency OLED employing $MoO_3$-doped CuPc as hole injection layer," *Displays*, 33(1): 17-20 (2012); Wen et al., "Self-assembled of conducting polymeric nanoparticles and its application for OLED hole injection layer," *Energy Procedia*, 12: 609-614 (2011); Zhang et al., "Role of $Fe_3O_4$ as a p-dopant in improving the hole injection and transport of organic light-emitting devices," *IEEE Journal of Quantum Electronics*, 47(5): 591-596 (2011); Choo et al., "Luminance and charge transport mechanisms for phosphorescent organic light-emitting devices fabricated utilizing a tris(2-phenylpyridine)iridium-doped N,N'-dicarbazolyl-3,5-benzene emitting layer," *Thin Solid Films*, 519(15): 5253-5256 (2011); Tao et al., "Odd-even modulation of electrode work function with self-assembled layer: Interplay of energy barrier and tunneling distance on charge injection in organic light-emitting diodes," *Organic Electronics*, 12(4): 602-608 (2011); Sung et al., "AC Field-Induced Polymer Electroluminescence with Single Wall Carbon Nanotubes," *Nano Letters*, 11(3): 966-972 (2011); Qiao et al., "Controlling charge balance and exciton recombination by bipolar host in single-layer organic light-emitting diodes," *Journal of Applied Physics*, 108(3): 034508/1-034508/8 (2011); Khizar-ul-Haq et al., "Blue organic light-emitting diodes with low driving voltage and enhanced power efficiency based on $MoO_3$ as hole injection layer and optimized charge balance," *Journal of Non-Crystalline Solids*, 356(20-22): 1012-1015 (2010); Qi et al., "Analysis of metal-oxide-based charge generation layers used in stacked organic light-emitting diodes," *Journal of Applied Physics*, 107(1): 014514/1-014514/8 (201); Huang et al., "Materials and interface engineering in organic light-emitting diodes," *Organic Electronics*, 243-261 (2010); Helander et al., "Comparison of Alq₃/alkali-metal fluoride/Al cathodes for organic electroluminescent devices," *Journal of Applied Physics*, 104(9): 094510/1-094510/6 (2008); Roy Choudhury et al., "LiF as an n-dopant in tris(8-hydroxyquinoline) aluminum thin films," *Advanced Materials*, 20(8): 1456-1461 (2008); Vacca et al., "Poly(3,4-ethylenedioxythiophene):poly(4-styrenesulfonate) ratio: Structural, physical and hole injection properties in organic light emitting diodes," *Thin Solid Films*, 516(12): 4232-4237 (2008); Yang et al., "Improved fabrication process for enhancing light emission in single-layer organic light-emitting devices doped with organic salt," Japanese Journal of Applied Physics, 47(2, Pt. 1): 1101-1103 (2008); Kim et al., "UV-ozone surface treatment of indium-tin-oxide in organic light emitting diodes," Journal of the Korean Physical Society, 50(6): 1858-1861 (2007); Prat et al., "Stable, highly efficient and temperature resistant organic light-emitting devices," *Japanese Journal of Applied Physics, Part 1: Regular Papers, Brief Communications & Review Papers,* 46(4A): 1727-1730 (2007); Luo et al., "Improving the stability of organic light-emitting devices by using a hole-injection-tunable-anode-buffer-layer," *Journal of Applied Physics*, 101(5): 054512/1-054512/4 (2007); Matsushima et al., "Charge-carrier injection characteristics at organic/organic heterojunction interfaces in organic light-emitting diodes," *Chemical Physics Letters*, 435(4-6): 327-330 (2007); Kim et al., "Controllable work function of Li—Al alloy nanolayers for organic light-emitting devices," *Advanced Engineering Materials*, 7(11): 1023-1027 (2005); Kato, "Designing Interfaces That Function to Facilitate Charge Injection in Organic Light-Emitting Diodes," *Journal of the American Chemical Society*, 127(33): 11538-11539 (2005); Veinot et al., "Toward the Ideal Organic Light-Emitting Diode. The Versatility and Utility of Interfacial Tailoring by Cross-Linked Siloxane Interlayers," *Accounts of Chemical Research*, 38(8): 632-643 (2005); Oyamada et al., "Extremely low-voltage driving of organic light-emitting diodes with a Cs-doped phenyldipyrenylphosphine oxide layer as an electron-injection layer," *Applied Physics Letters*, 86(3): 033503/1-033503/3 (2005); Hughes et al., "Electron-transporting materials for organic electroluminescent and electrophosphorescent devices," *Journal of Materials Chemistry*, 15(1): 94-107 (2005); D'Andrade et al., "Efficient organic electrophosphorescent white-light-emitting device with a triple doped emissive layer," *Advanced Materials*, 16(7): 624-628 (2004); Kanno et al., "Development of OLED with high stability and luminance efficiency by co-doping methods for full color displays," *IEEE Journal of Selected Topics in Quantum Electronics*, 10(1): 30-36 (2004); Han et al., "Transparent-cathode for top-emission organic light-emitting diodes," *Applied Physics Letters*, 82(16): 2715-2717 (2003); Tutis et al., "Internal electric field and charge distribution in multilayer organic light-emitting diodes," *Journal of Applied Physics*, 93(8): 4594-4602 (2003); Mathai et al., "Controlled injection of holes into AlQ3 based OLEDs by means of an oxidized transport layer," *Materials Research Society Symposium Proceedings*, 708 (Organic Optoelectronic Materials, Processing and Devices): 101-106 (2002); Crone et al., "Charge injection and transport in single-layer organic light-emitting diodes," *Applied Physics Letters*, 73(21): 3162-3164 (1998); and Park et al., "Charge injection and photooxidation of single conjugated polymer molecules," *Journal of the American Chemical Society*, 126(13): 4116-7 (2004).

OLETs according to the present teachings can be fabricated on various substrates including plastic, flexible substrates that have a low temperature resistance. Examples of such flexible substrates include polyesters such as polyethylene terephthalate, polyethylene naphthalate, polycarbonate; polyolefins such as polypropylene, polyvinyl chloride, and polystyrene; polyphenylene sulfides such as polyphenylene sulfide; polyamides; aromatic polyamides; polyether ketones; polyimides; acrylic resins; polymethylmethacrylate, and blends and/or copolymers thereof. In some embodiments, the substrate can be a rigid transparent substrate such as glass, quartz and VYCOR®. Substrate-gate materials commonly used in thin-film transistors also can be used. Examples include doped silicon wafer, tin-doped indium oxide (ITO) on glass, tin-doped indium oxide on polyimide or mylar film, aluminum or other metals alone or coated on a polymer such as polyethylene terephthalate, a doped polythiophene, and the like.

The thicknesses of the various layers may be adapted in order to optimize performances and scaling down of the electroluminescent transistor of this disclosure. In this regard it is preferable to have the thickness of the layer of p-type semiconductor material comprised between 5 and 50 nm, preferably between 15 and 45 nm, the thickness of the layer of n-type semiconductor material may be comprised between 30 nm and 60 nm and the thickness of the layer of emissive material may be comprised between 30 nm and 60 nm.

A plurality of OLETs can be arranged in a matrix to provide a display device. The display device can include optional driving and switching elements, compensating transistor elements, capacitors, and/or light-emitting diodes. Particularly, such optional driving and switching elements and compensating transistor elements can be organic field-effect transistors.

The following examples are provided to illustrate further and to facilitate understanding of the present disclosure and are not in any way intended to limit the invention.

Acronyms are used in the examples to represent certain chemical compounds. Table 1 below provides the IUPAC names and the acronyms of such compounds.

TABLE 1

| | |
|---|---|
| C8-BTBT | 2,7-dioctyl[1]benzo-thieno[3,2-b][1]benzothiophene |
| C5-BTBT | 2,7-dipentyl[1]benzo-thieno[3,2-b][1]benzothiophene |
| DNTT | dinaphtho[2,3-b:2',3'-f]thieno[3,2-b]thiophene |
| DH4T | 5,5'-bis(3-hexyl-2-thienyl)-2,2'-bithiophene |
| N-F2-6 | 2,5-bis(4-(perfluorooctyl)phenyl)thieno[3,2-b]thiophene |
| N-F2-6-CF3 | 2,5-bis(4-(trifluoromethyl)phenyl)thieno[3,2-b]thiophene |
| N-F4-1 | 2,6-bis(4-heptadecafluorooctylphenyl)-dithieno[3,2-b:2',3'-d]thiophene |
| DFH4T | 5,5'-bis((5-perfluorohexyl)thiophen-2-yl)-2,2'-bithiophene |
| TCTA | 4,4',4"-tris(carbazole-9-yl)triphenylamine |
| NP4-CBP | 4,4'-bis(3,6-dineopentyl-9H-carbazole-9-yl)-1,1'-biphenyl |
| Ir(piq)₃ | tris(1-phenylisoquinoline)iridium(III) |
| Ir(ppy)₃ | tris(2-phenylpyridine)iridium(III) |
| FIrpic | bis(4,6-difluorophenyl-pyridine)(picolinate)iridium(III) |
| PtOEP | 2,3,7,8,12,13,17,18-octaethylporphyrin-22,24-diide; platinum(2+) |
| Alq₃ | tris(8-hydroxyquinolinato)aluminium |
| DCM | 4-(dicyanomethylene)-2-methyl-6-(4-dimethylaminostyryl)-4H-pyran |

Example 1

With reference to FIG. 1, an organic ambipolar light-emitting transistor (OLET) according to the present teachings was fabricated on a glass substrate (first layer 1), onto which a transparent control electrode 2 made of ITO (indium tin oxide) was provided. A 450 nm-thick dielectric layer 3 composed of poly(methyl methacrylate) (PMMA) was fabricated on the ITO electrode by spin-coating and cured in vacuum at 90° C. An organic emissive ambipolar channel was formed on the dielectric layer by sublimation in vacuum ($10^{-7}$ mbar) and includes the following layers:

a hole transport layer 4 composed of a p-type semiconductor material deposited over the dielectric layer 3, specifically, a 15 nm-thick film made of C8-BTBT sublimated at a rate of 0.1 Å/s, while the substrate was maintained at room temperature;

an emissive layer 5 in contact with the hole transport layer 4, specifically, a 60 nm-thick recombination layer composed of a host-guest system (with a guest emitter concentration of 20%). TCTA was used as the host matrix and it was sublimated at a rate of 1 Å/s, while the substrate was maintained at room temperature. Ir(piq)$_3$ was used as the guest emitter and it was sublimated at a rate of 0.25 Å/s, while the substrate was maintained at room temperature; and an electron transport layer 6 in contact with the emissive layer 5, specifically, a 45 nm-thick film of N-F2-6 sublimated at a rate of 0.1 Å/s, while the substrate was maintained at room temperature.

The metal source and drain electrodes 7 and 7', made of silver (Ag), were deposited in vacuum ($10^{-6}$ mbar) and each has a thickness of 70 nm.

The device channel length (L) and channel width (W) are 70 μm and 12 mm, respectively.

The OLET described above was found to have the following characteristic parameters:
p-type threshold voltage=−40.1 V;
p-type mobility=$5.2 \times 10^{-1}$ cm$^2$/Vs;
n-type threshold voltage=38.4 V;
n-type mobility=$3.6 \times 10^{-3}$ cm$^2$/Vs.

Figure 2:
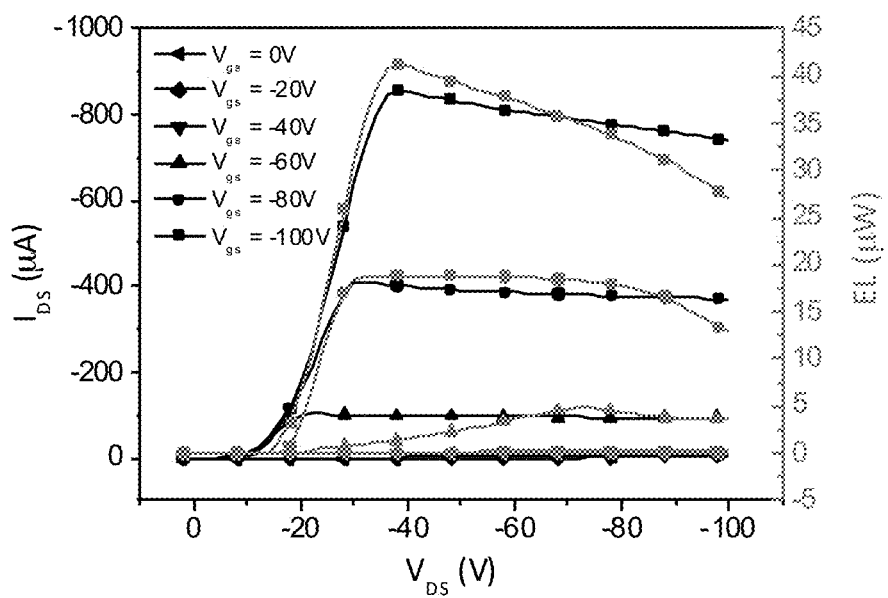
FIG. 2 plots drain-source current $I_{DS}$ (left scale—black curves) and electroluminescence optical output power EL (right scale—gray curves) as a function of the drain-source voltage $V_{DS}$ at different values of the gate-source voltage $V_{GS}$, as obtained from a first exemplary OLET having the architecture shown in FIG. 1 and incorporating a BTBT compound represented by formula (P-I) as the p-type semiconductor material.
Figure 3:
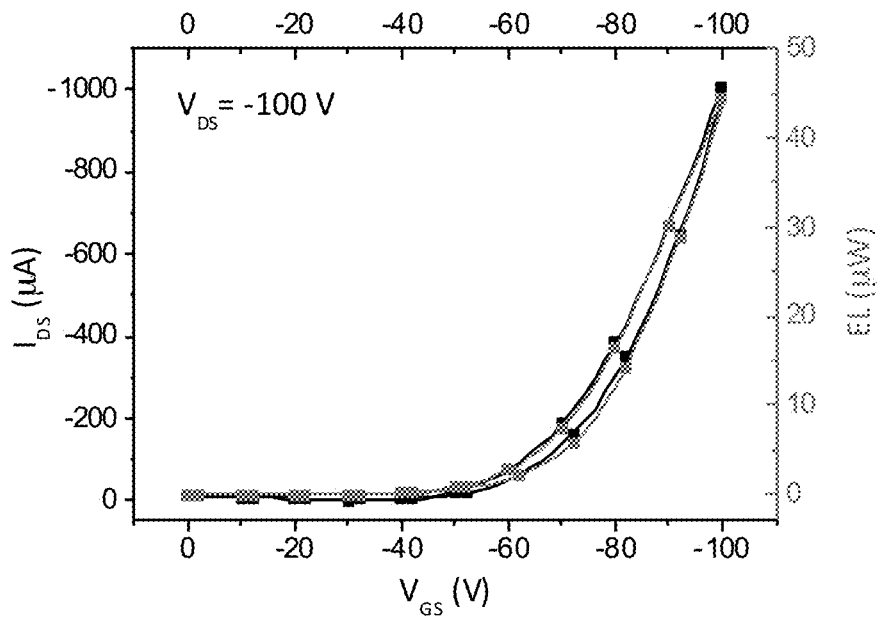
FIG. 3 plots drain-source current $I_{DS}$ (left scale—black curve) and electroluminescence optical output power EL (right scale—gray curve) as a function of the gate-source voltage $V_{GS}$ while the drain contact was maintained at a constant bias voltage of −100V and the source contact was grounded ($V_{DS}=-100V$), as obtained from the first exemplary OLET.

Current-voltage graphs of the tested OLET are shown in FIG. 2 and FIG. 3. FIG. 2 illustrates variations of the drain-source current ($I_{DS}$) (left scale—black curves) and the electroluminescence optical output power (EL) (right scale—gray curves) as a function of the drain-source voltage ($V_{DS}$) at different gate-source voltages ($V_{GS}$), while the source contact was grounded. FIG. 3 illustrates variations of the drain-source current ($I_{DS}$) (left scale—black curve) and of the electroluminescence optical output power (EL) (right scale—gray curve) as a function of the gate-source voltage ($V_{GS}$) while the drain contact was maintained at a constant bias voltage of −100V and the source contact was grounded ($V_{DS}$=−100V).

Figure 4:
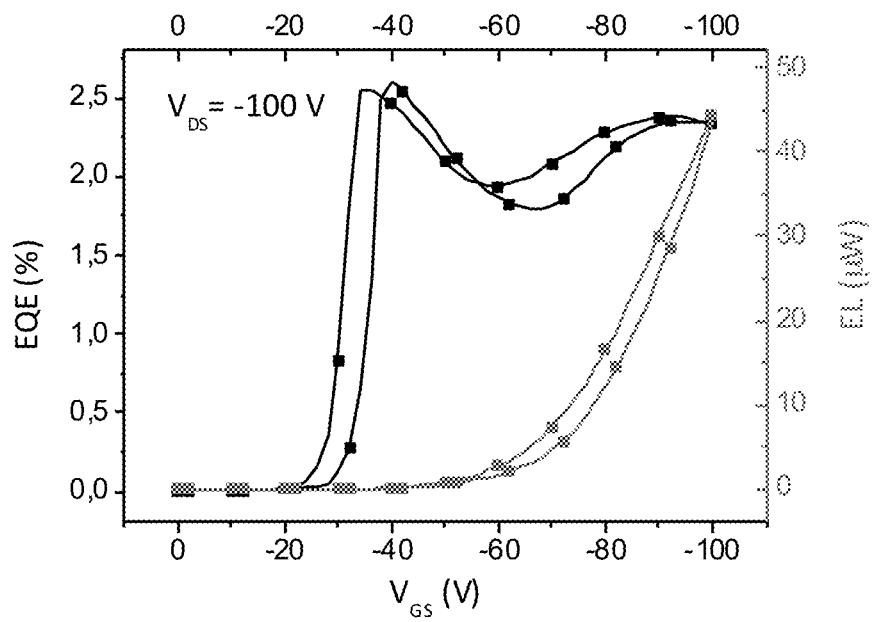
FIG. 4 plots external quantum efficiency EQE (left scale—black curves) and electroluminescence optical output power EL (right scale—gray curves) as a function of the gate-source voltage $V_{GS}$ while the drain contact was maintained at a constant bias voltage of −100V and the source contact was grounded ($V_{DS}=-100V$), as obtained from the first exemplary OLET.

FIG. 4 shows graphs of the external quantum efficiency (EQE, left scale—black curve) and of the electroluminescence optical output power EL (right scale—gray curves) as a function of the gate-source voltage $V_{GS}$ while the drain contact was maintained at a constant bias voltage of −100V and the source contact was grounded ($V_{DS}$=−100V).

As shown in FIG. 4, the tested OLET which has an organic emissive ambipolar channel that includes a hole transport layer composed of a BTBT compound (in this case, C8-BTBT) unexpectedly achieved maximum brightness (EL ~45 μW) and efficiency (EQE ~2.25%) simultaneously.

Example 2

A second OLET was fabricated in the same manner and using the same materials as the OLET described in Example 1, except that a different BTBT compound was used in the hole transport layer 4. Specifically, the hole transport layer 4 was composed of a 15 nm-thick film made of C5-BTBT instead of C8-BTBT.

The resulting OLET showed the following characteristic parameters:
p-type threshold voltage=−54.5 V;
p-type-mobility=$1.2 \times 10^{-1}$ cm$^2$/Vs;
n-type threshold voltage=25.9 V;
n-type mobility=$4.2 \times 10^{-3}$ cm$^2$/Vs.

Figure 5:
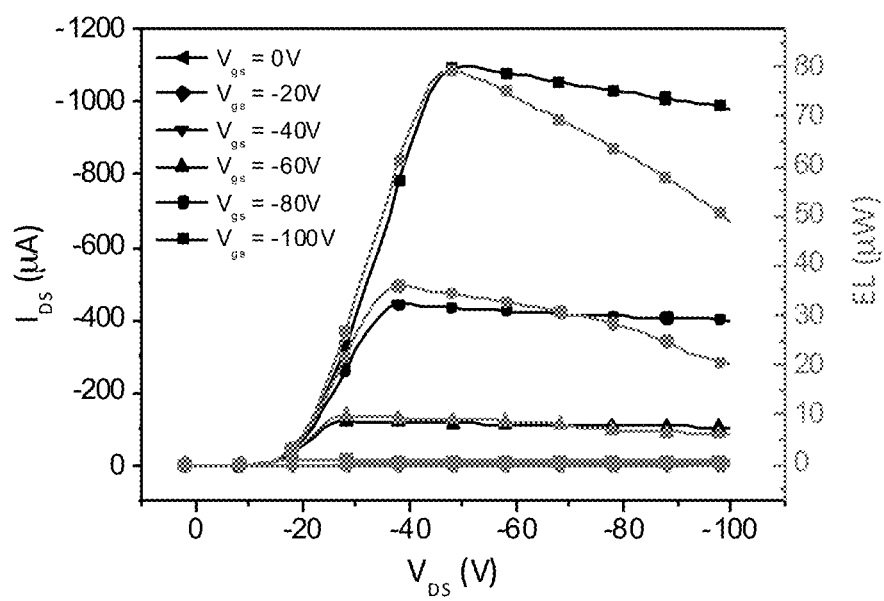
FIG. 5 plots drain-source current $I_{DS}$ (left scale—black curves) and electroluminescence optical output power EL (right scale—gray curves) as a function of the drain-source voltage $V_{DS}$ at different values of the gate-source voltage $V_{GS}$, as obtained from a second exemplary OLET having the architecture shown in FIG. 1 and incorporating a different BTBT compound represented by formula (P-I) as the p-type semiconductor material.
Figure 6:
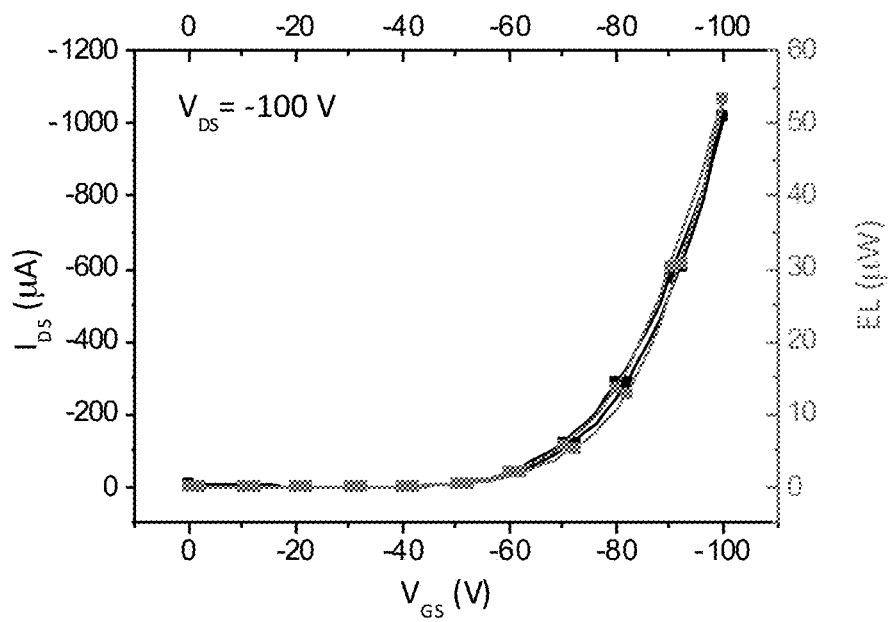
FIG. 6 plots drain-source current $I_{DS}$ (left scale—black curve) and electroluminescence optical output power EL (right scale—gray curve) as a function of the gate-source voltage $V_{GS}$ while the drain contact was maintained at a constant bias voltage of −100V and the source contact was grounded ($V_{DS}=-100V$), as obtained from the second exemplary OLET.

Current-voltage graphs of the tested OLET are shown in FIG. 5 and FIG. 6. FIG. 5 illustrates variations of the drain-source current ($I_{DS}$) (left scale—black curves) and the electroluminescence optical output power (EL) (right scale—gray curves) as a function of the drain-source voltage ($V_{DS}$) at different gate-source voltage ($V_{GS}$), while the source contact was grounded. FIG. 6 illustrates variations of the drain-source current ($I_{DS}$) (left scale—black curve) and of the electroluminescence optical output power (EL) (right scale—gray curve) as a function of the gate-source voltage ($V_{GS}$) while the drain contact was maintained at a constant bias voltage of −100V and the source contact was grounded ($V_{DS}$=−100V).

Figure 7:
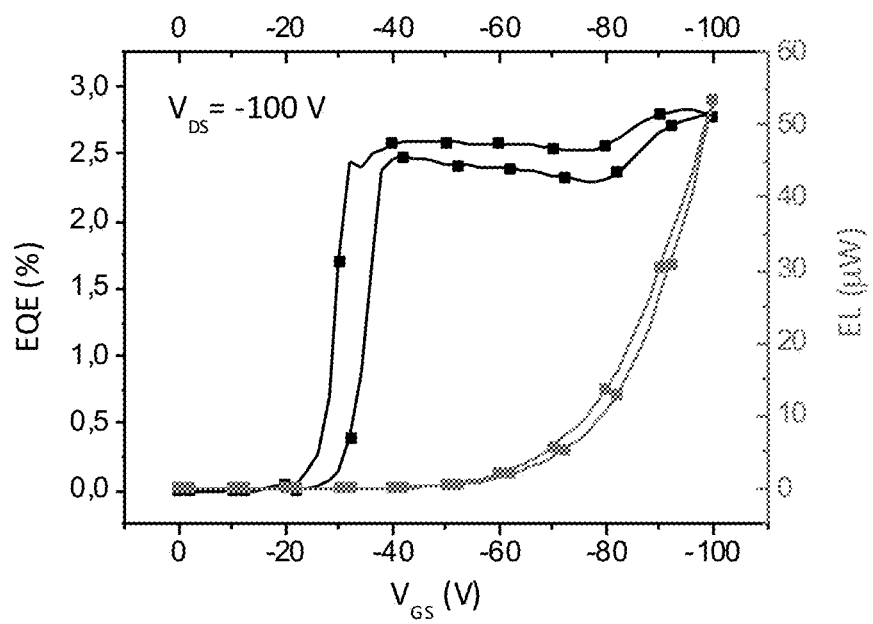
FIG. 7 plots external quantum efficiency EQE (left scale—black curves) and electroluminescence optical output power EL (right scale—gray curves) as a function of the gate-source voltage $V_{GS}$ while the drain contact was maintained at a constant bias voltage of −100V and the source contact was grounded ($V_{DS}=-100V$), as obtained from the second exemplary OLET.

FIG. 7 shows graphs of the external quantum efficiency (EQE, left scale—black curve) and of the electroluminescence optical output power EL (right scale—gray curves) as a function of the gate-source voltage $V_{GS}$ while the drain contact was maintained at a constant bias voltage of −100V and the source contact was grounded ($V_{DS}$=−100V).

As shown in FIG. 7, the tested OLET which has an organic emissive ambipolar channel that includes a hole transport layer composed of a BTBT compound (in this case, C5-BTBT) unexpectedly achieved maximum brightness (EL>50 μW) and efficiency (EQE>2.5%) simultaneously.

Example 3 (Comparative)

The comparative device tested in this example incorporated a DNTT compound as the p-type semiconductor material in the hole transport layer 4. Previous reports have suggested that DNTT compounds (which have naphthalene, i.e., 2 benzene rings, fused to each side of the thienothiophene center) can achieve higher mobilities than BTBT compounds (which have only 1 benzene ring fused to each side of the thienothiophene center) despite their structural similarity. See e.g., M. J. Kang et al., "Two Isomeric Didecyl-dinaphtho[2,3-b:2',3'-f]thieno[3,2-b]thiophenes: Impact of Alkylation Positions on Packing Structures and Organic Field Effect Transistor Characteristics," *Jpn. J. Appl. Phys.*, vol. 51, pp. 11PD04 (2012); and H. Ebata et al., "Highly Soluble [1]Benzothieno[3,2-b]benzothiophene (BTBT) Derivatives for High-Performance, Solution-Processed Organic Field-Effect Transistors," *J. Am. Chem. Soc.*, vol. 129, pp. 15732-15733 (2007).

Specifically, the comparative OLET was fabricated in the same manner and using the same materials as the OLET described in Example 1, except that the hole transport layer 4 was composed of a 15 nm-thick film made of DNTT instead of C8-BTBT.

The resulting transistor showed the following characteristic parameters:
p-type threshold voltage=−40 V;
p-type-mobility=$5 \times 10^{-5}$ cm$^2$/Vs;
n-type threshold voltage=34 V;
n-type mobility=0.5 cm$^2$/Vs.

Figure 8:
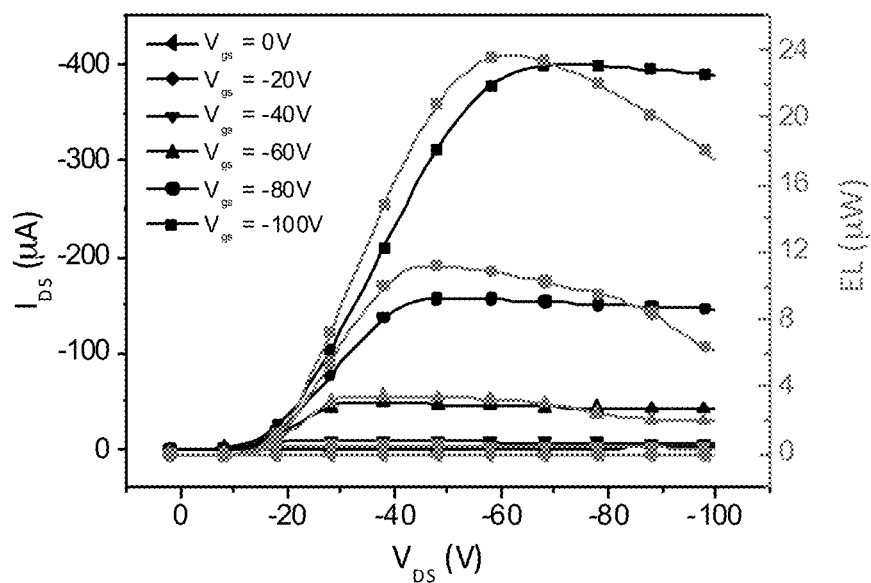
FIG. 8 plots drain-source current $I_{DS}$ (left scale—black curves) and electroluminescence output power EL (right scale—gray curves) as a function of the drain-source voltage $V_{DS}$ at different values of the gate-source voltage $V_{GS}$, as obtained from a first comparative OLET having the architecture shown in FIG. 1 and incorporating a comparative hole-transporting compound (DNTT) that is structurally similar to a BTBT compound but not within formula (P-I) as the p-type semiconductor material.
Figure 9:
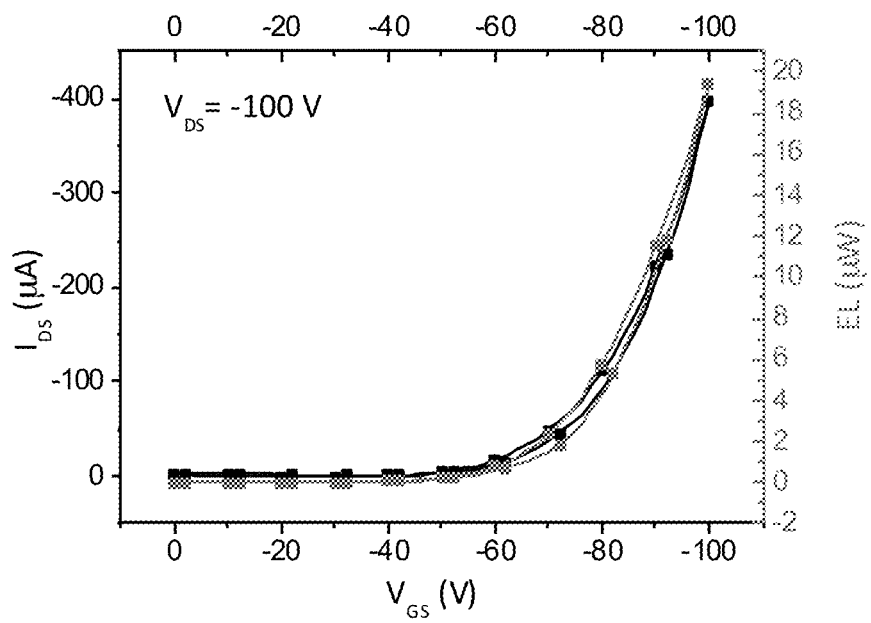
FIG. 9 plots drain-source current $I_{DS}$ (left scale—black curve) and electroluminescence optical output power EL (right scale—gray curve) as a function of the gate-source voltage $V_{GS}$ while the drain contact was maintained at a constant bias voltage of −100V and the source contact was grounded ($V_{DS}=-100V$), as obtained from the first comparative OLET.

Current-voltage graphs of the tested OLET are shown in FIG. 8 and FIG. 9. FIG. 8 illustrates variations of the drain-source current ($I_{DS}$) (left scale—black curves) and the electroluminescence optical output power (EL) (right scale—gray curves) as a function of the drain-source voltage ($V_{DS}$) at different gate-source voltage ($V_{GS}$), while the source contact was grounded. FIG. 9 illustrates variations of the drain-source current ($I_{DS}$) (left scale—black curve) and of the electroluminescence optical output power (EL) (right scale—gray curve) as a function of the gate-source voltage ($V_{GS}$) while the drain contact was maintained at a constant bias voltage of −100V and the source contact was grounded ($V_{DS}$=−100V).

Figure 10:
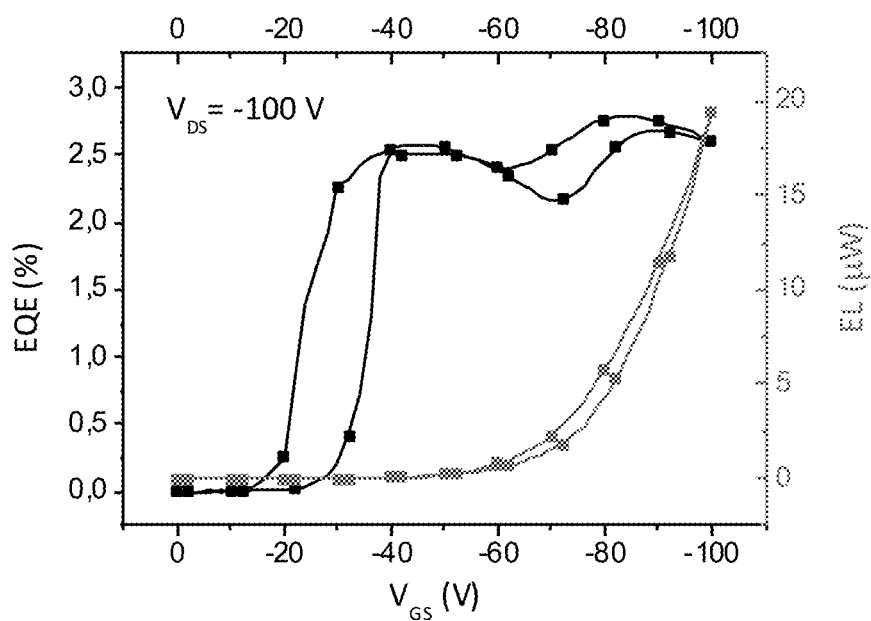
FIG. 10 plots external quantum efficiency EQE (left scale—black curves) and electroluminescence optical output power EL (right scale—gray curves) as a function of the gate-source voltage $V_{GS}$ while the drain contact was maintained at a constant bias voltage of −100V and the source contact was grounded ($V_{DS}=-100V$), as obtained from the first comparative OLET.

FIG. 10 shows graphs of the external quantum efficiency (EQE, left scale—black curve) and of the electroluminescence optical output power EL (right scale—gray curves) as a function of the gate-source voltage $V_{GS}$ while the drain contact was maintained at a constant bias voltage of −100V and the source contact was grounded ($V_{DS}$=−100V).

As shown in FIG. 10, although the tested DNTT-based OLET was able to achieve maximum brightness (EL ~20 µW) and efficiency (EQE ~2.5%) simultaneously like the BTBT-based OLETs, the electroluminescence achieved by the DNTT-based OLET was less than 50% of the electroluminescence achieved by the BTBT-based OLETs (which was EL ~45 µW, and EL>50 µW, respectively).

The significantly higher EL values observed with the BTBT-based OLETs are surprising given that DNTT compounds have been shown to exhibit comparable, if not higher, mobilities, compared to BTBT compounds in the literature.

Example 4 (Comparative)

The comparative OLET device tested in this example incorporated the p-type semiconductor material (DH4T), the n-type semiconductor material (DFH4T, a bis(fluoroalkyl-substituted) oligothiophene), and the emissive material (Alq$_3$:DCM) used in the organic light-emitting transistor reported in R. Capelli et al., "Organic light-emitting transistors with an efficiency that outperforms the equivalent light-emitting diodes," *Nature Materials*, vol. 9, pp. 496-503 (2010).

Specifically, and with reference again to FIG. 1, a comparative OLET was fabricated on a glass substrate (first layer 1), onto which a transparent control electrode 2 made of ITO (indium tin oxide) was provided. A 450 nm-thick dielectric layer 3 composed of poly(methyl methacrylate) (PMMA) was fabricated on the ITO electrode by spin-coating and cured in vacuum at 90° C. An organic emissive ambipolar channel was formed on the dielectric layer by sublimation in vacuum ($10^{-7}$ mbar) and includes the following layers:

an electron transport layer 4 of an n-type semiconductor material deposited over the dielectric layer 3, specifically, a layer of 15 nm-thick film made of DFH4T sublimated at a rate of 0.1 Å/s, while the substrate was maintained at room temperature;

an emissive layer 5 in contact with the hole transport layer 4, specifically, a 60 nm-thick recombination layer composed of a host-guest system (with a guest emitter concentration of 20%). Alq$_3$ was used as the host matrix and it was sublimated at a rate of 1 Å/s, while the substrate was maintained at room temperature. DCM was used as the guest emitter and it was sublimated at a rate of 0.25 Å/s, while the substrate was maintained at room temperature; and a hole transport layer 6 in contact with the emissive layer 5, in this case, a 45 nm-thick film of DH4T sublimated at a rate of 0.1 Å/s, while the substrate was maintained at room temperature.

The metal source and drain electrodes 7 and 7', made of silver (Ag), were deposited in vacuum ($10^{-6}$ mbar) and each has a thickness of 70 nm.

The device channel length (L) and channel width (W) are 70 µm and 12 mm, respectively.

The resulting OLET was found to have the following characteristic parameters:

p-type threshold voltage=−60 V;
p-type mobility=5.3×10$^{-1}$ cm$^2$/Vs;
n-type threshold voltage=23.7 V;
n-type mobility=3.6×10$^{-3}$ cm$^2$/Vs.

Figure 11:
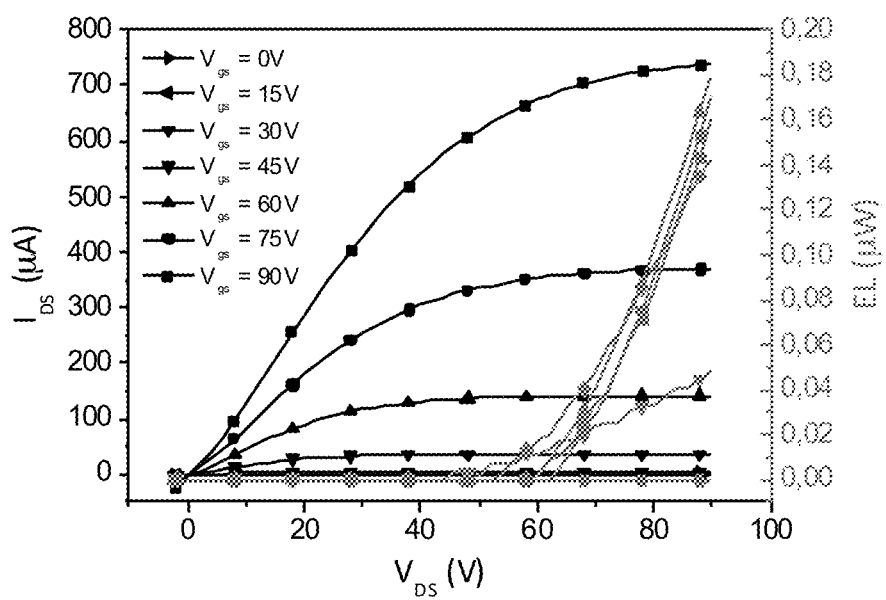
FIG. 11 plots drain-source current $I_{DS}$ (left scale—black curves) and electroluminescence output power EL (right scale—gray curves) as a function of the drain-source voltage $V_{DS}$ at different values of the gate-source voltage $V_{GS}$, as obtained from a second comparative OLET having the architecture shown in FIG. 1 and incorporating a comparative hole-transporting compound previously reported in the literature that is not within formula (P-I) as the p-type semiconductor material.
Figure 12:
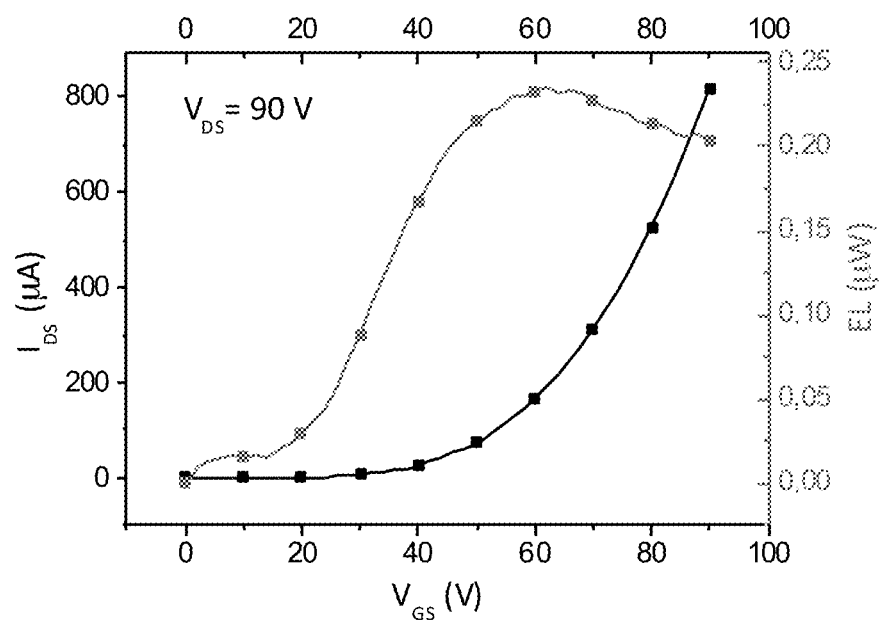
FIG. 12 plots drain-source current $I_{DS}$ (left scale—black curve) and electroluminescence optical output power EL (right scale—gray curve) as a function of the gate-source voltage $V_{GS}$ while the drain contact was maintained at a constant bias voltage of −100V and the source contact was grounded ($V_{DS}=-100V$), as obtained from the second comparative OLET.

Current-voltage graphs of the tested OLET are shown in FIG. 11 and FIG. 12. FIG. 11 illustrates variations of the drain-source current ($I_{DS}$) (left scale—black curves) and the electroluminescence optical output power (EL) (right scale—gray curves) as a function of the drain-source voltage ($V_{DS}$) at different gate-source voltage ($V_{GS}$), while the source contact was grounded. FIG. 12 illustrates variations of the drain-source current ($I_{DS}$) (left scale—black curve) and of the electroluminescence optical output power (EL) (right scale—gray curve) as a function of the gate-source voltage ($V_{GS}$) while the drain contact was maintained at a constant bias voltage of 90V and the source contact was grounded ($V_{DS}$=90V).

Figure 13:
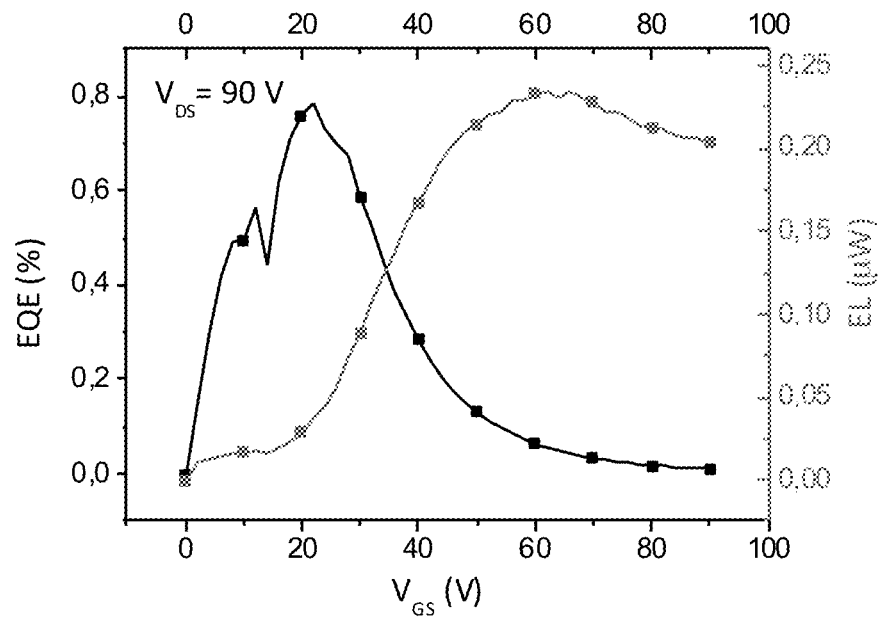
FIG. 13 plots external quantum efficiency EQE (left scale—black curves) and electroluminescence optical output power EL (right scale—gray curves) as a function of the gate-source voltage $V_{GS}$ while the drain contact was maintained at a constant bias voltage of −100V and the source contact was grounded ($V_{DS}=-100V$), as obtained from the second comparative OLET.

FIG. 13 shows graphs of the external quantum efficiency (EQE, left scale—black curve) and of the electroluminescence optical output power EL (right scale—gray curves) as a function of the gate-source voltage $V_{GS}$ while the drain contact was maintained at a constant bias voltage of 90V and the source contact was grounded ($V_{DS}$=90V).

As shown in FIG. 13, the comparative OLET tested in this example, which incorporated a combination of materials previously reported in the art, showed significantly lower brightness (EL <0.25 µW) and efficiency (EQE <0.8%) compared to the devices of Examples 1 and 2. Further, the maximum brightness was obtained under conditions when the efficiency was very low, and vice versa (as indicated by the inverse relationship of the EQE and EL curves, especially between $V_{GS}$=20 V and $V_{GS}$=60 V).

Example 5

Another aspect of the present teachings is directed to the use of an emissive material in a trilayer OLET device, where the emissive material is a blend including an organic arylamine matrix compound (H-1) or (H-2) and an iridium-based emitter selected from (G-1), (G-2), and (G-3).

Referring to FIG. 1, an organic ambipolar light-emitting transistor (OLET) according to the present teachings was fabricated on a glass substrate (first layer 1), onto which a transparent control electrode 2 made of ITO (indium tin oxide) was provided. A 450 nm-thick dielectric layer 3 composed of poly(methyl methacrylate) (PMMA) was fabricated on the ITO electrode by spin-coating and cured in vacuum at 90° C. An organic emissive ambipolar channel was formed on the dielectric layer by sublimation in vacuum ($10^{-7}$ mbar) and includes the following layers:

a hole transport layer 4 composed of a p-type semiconductor material deposited over the dielectric layer 3, specifically, a 45 nm-thick film made of DH4T sublimated at a rate of 0.1 Å/s, while the substrate was maintained at room temperature;

an emissive layer 5 in contact with the hole transport layer 4, specifically, a 60 nm-thick recombination layer composed of a host-guest system (with a guest emitter concentration of 20%). TCTA was used as the host matrix and it was sublimated at a rate of 1 Å/s, while the substrate was maintained at room temperature. Ir(piq)$_3$ was used as the guest emitter and it was sublimated at a rate of 0.25 Å/s, while the substrate was maintained at room temperature; and an electron transport layer 6 in contact with the emissive layer 5, specifically, a 45 nm-thick film of N-F4-1 sublimated at a rate of 0.1 Å/s, while the substrate was maintained at room temperature.

The metal source and drain electrodes 7 and 7', made of silver (Ag), were deposited in vacuum ($10^{-6}$ mbar) and each has a thickness of 70 nm.

The device channel length (L) and channel width (W) are 70 μm and 12 mm, respectively.

The OLET described above was found to have the following characteristic parameters:
p-type threshold voltage=−49 V;
p-type mobility=$1.3 \times 10^{-1}$ cm$^2$/Vs;
n-type threshold voltage=null;
n-type mobility=null.

Figure 14:
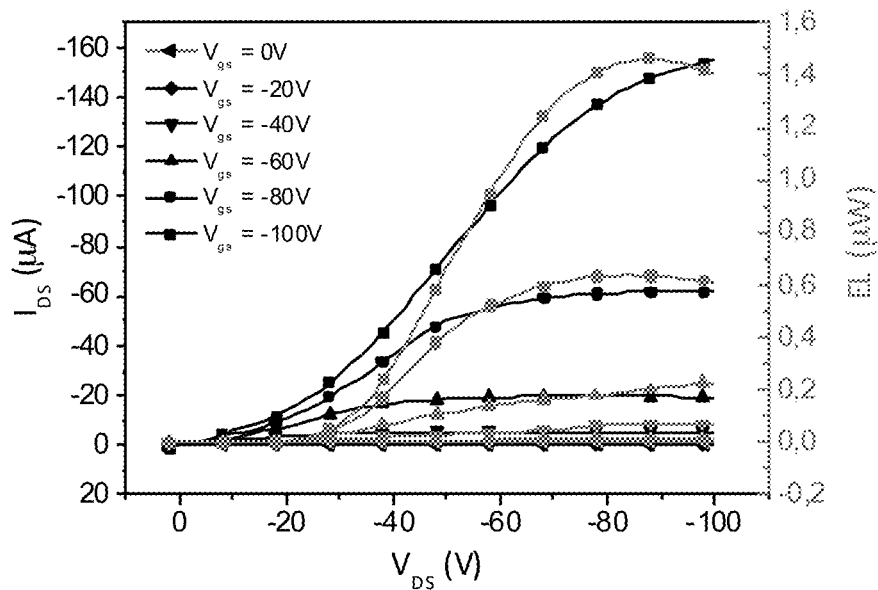
FIG. 14 plots drain-source current $I_{DS}$ (left scale—black curves) and electroluminescence optical output power EL (right scale—gray curves) as a function of the drain-source voltage $V_{DS}$ at different values of the gate-source voltage $V_{GS}$, as obtained from a third exemplary OLET having the architecture shown in FIG. 1 and incorporating a blend material including an organic carbazole-based host matrix compound and an iridium complex guest emitter as the emissive layer.
Figure 15:
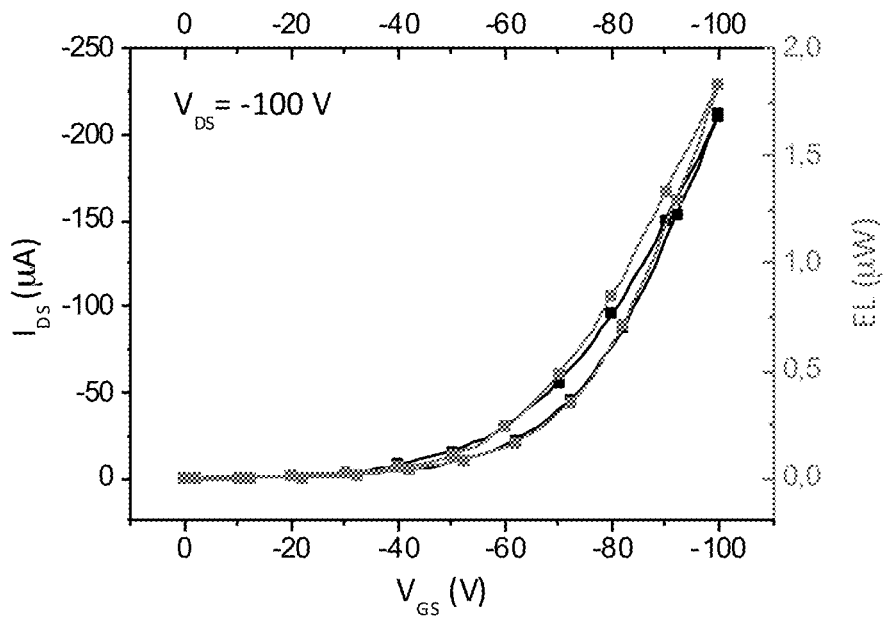
FIG. 15 plots drain-source current $I_{DS}$ (left scale—black curve) and electroluminescence optical output power EL (right scale—gray curve) as a function of the gate-source voltage $V_{GS}$ while the drain contact was maintained at a constant bias voltage of −100V and the source contact was grounded ($V_{DS}=-100V$), as obtained from the third exemplary OLET.

Current-voltage graphs of the tested OLET are shown in FIG. 14 and FIG. 15. FIG. 14 illustrates variations of the drain-source current ($I_{DS}$) (left scale—black curves) and the electroluminescence optical output power (EL) (right scale—gray curves) as a function of the drain-source voltage ($V_{DS}$) at different gate-source voltages ($V_{GS}$), while the source contact was grounded. FIG. 15 illustrates variations of the drain-source current ($I_{DS}$) (left scale—black curve) and of the electroluminescence optical output power (EL) (right scale—gray curve) as a function of the gate-source voltage ($V_{GS}$) while the drain contact was maintained at a constant bias voltage of −100V and the source contact was grounded ($V_{DS}$=−100V).

Figure 16:
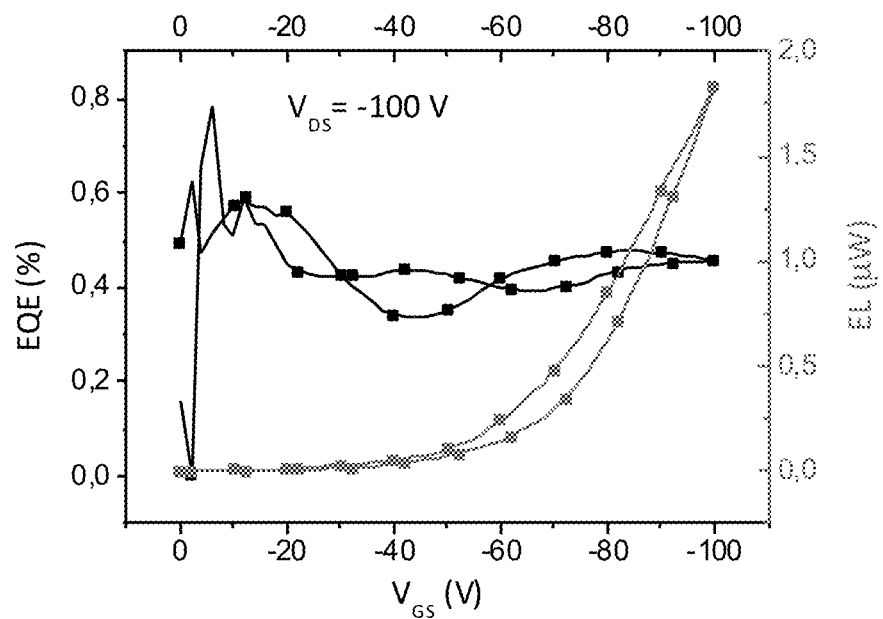
FIG. 16 plots external quantum efficiency EQE (left scale—black curves) and electroluminescence optical output power EL (right scale—gray curves) as a function of the gate-source voltage $V_{GS}$ while the drain contact was maintained at a constant bias voltage of −100V and the source contact was grounded ($V_{DS}=-100V$), as obtained from the third exemplary OLET.

FIG. 16 shows graphs of the external quantum efficiency (EQE, left scale—black curve) and of the electroluminescence optical output power EL (right scale—gray curves) as a function of the gate-source voltage $V_{GS}$ while the drain contact was maintained at a constant bias voltage of −100V and the source contact was grounded ($V_{DS}$=−100V).

As shown in FIG. 16, the tested OLET which has an emissive layer within the trilayer channel that includes a blend material composed of TCTA:Ir(piq)$_3$, i.e., the carbazole derivative TCTA as the host matrix compound and the iridium complex Ir(piq)$_3$ as the guest emitter, unexpectedly achieved maximum brightness (EL ~2 μW) and efficiency (EQE>0.4%) simultaneously.

Example 6 (Comparative)

In this example, a comparative OLET device was fabricated in the same manner and using the same materials as the OLET described in Example 5, except that a different blend material was used in the emissive layer 5. Specifically, the emissive layer 5 was a blend material composed of Alq$_3$:PtOEP, that is, both the host matrix and the guest emitter are metal complexes, and the guest emitter is a platinum-based complex instead of an iridium-based complex.

The resulting OLET showed the following characteristic parameters:
p-type threshold voltage=−55.2 V;
p-type-mobility=$3.8 \times 10^{-2}$ cm$^2$/Vs;
n-type threshold voltage=null;
n-type mobility=null.

Figure 17:
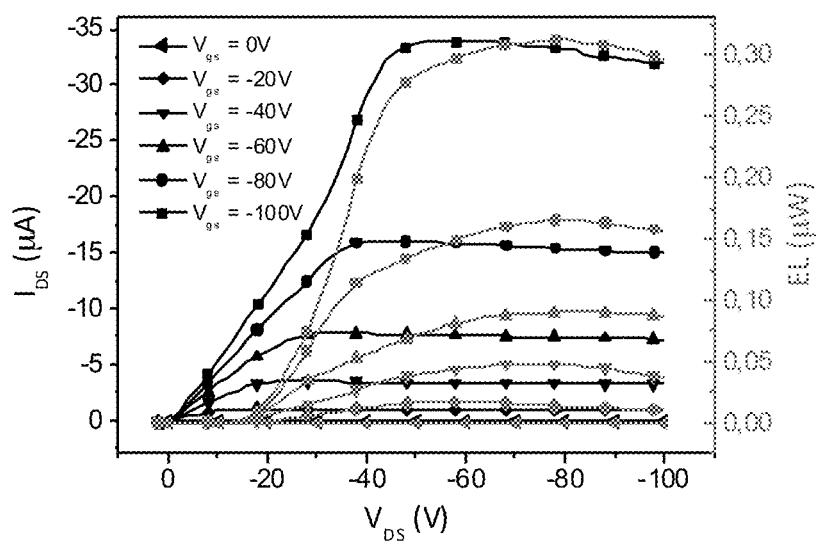
FIG. 17 depicts graphs of the drain-source current $I_{DS}$ (left scale—black curves) and of the electro-luminescence optical output power EL (right scale—gray curves) as a function of the drain-source voltage $V_{ts}$ at different values of the gate-source voltage $V_{GS}$, for a third comparative electroluminescent transistor not according to the present teachings. Specifically, the emissive layer is composed of a blend material including a metal complex host matrix compound and a platinum-based guest emitter.
Figure 18:
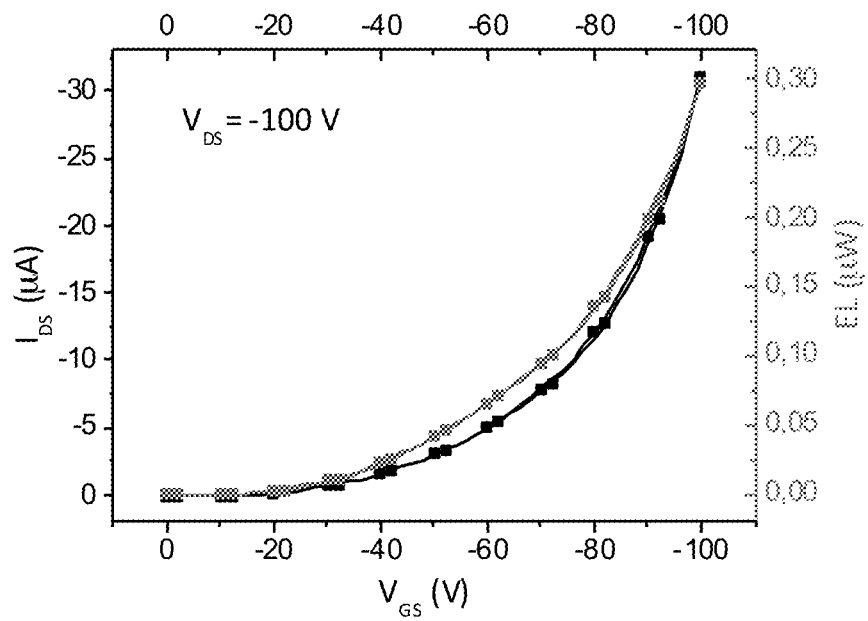
FIG. 18 depicts graphs of the drain-source current $I_{DS}$ (left scale—black curve) and of the electro-luminescence optical output power EL (right scale—gray curves) in function of the gate-source voltage $V_{GS}$ whilst the drain contact was maintained at a constant bias voltage of −100V and the source contact was grounded ($V_{DS}=-100V$), for the third comparative electroluminescent transistor.

Current-voltage graphs of the tested OLET are shown in FIG. 17 and FIG. 18. FIG. 17 illustrates variations of the drain-source current ($I_{DS}$) (left scale—black curves) and the electroluminescence optical output power (EL) (right scale—gray curves) as a function of the drain-source voltage ($V_{DS}$) at different gate-source voltage ($V_{GS}$), while the source contact was grounded. FIG. 18 illustrates variations of the drain-source current ($I_{DS}$) (left scale—black curve) and of the electroluminescence optical output power (EL) (right scale—gray curve) as a function of the gate-source voltage ($V_{GS}$) while the drain contact was maintained at a constant bias voltage of −100V and the source contact was grounded ($V_{DS}$=−100V).

Figure 19:
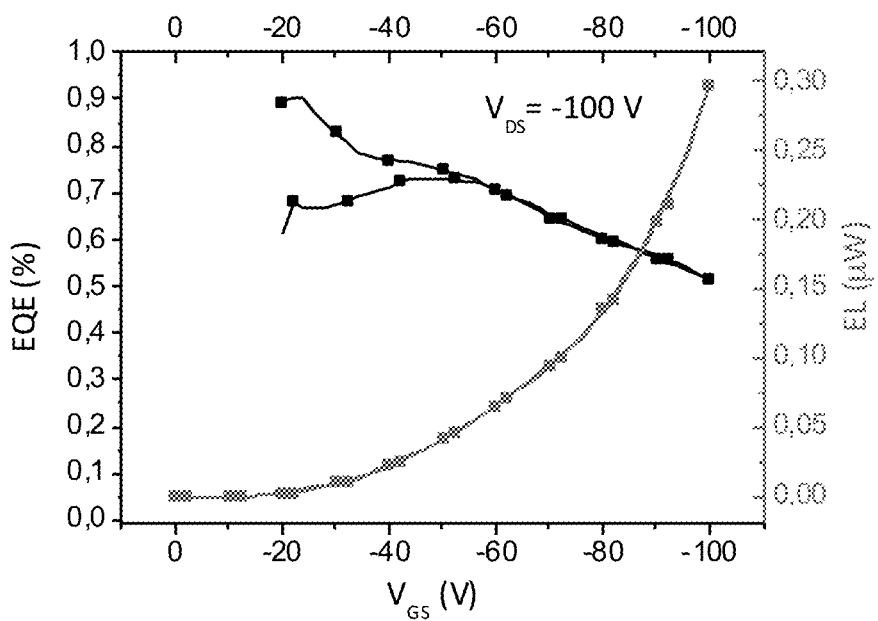
FIG. 19 depicts graphs of the external quantum efficiency (left scale—black curve) and of the electro-luminescence optical output power EL (right scale—gray curves) as a function of the gate-source voltage $V_{GS}$ whilst the drain contact was maintained at a constant bias voltage of −100V and the source contact was grounded ($V_{DS}=-100V$), for the third comparative electroluminescent transistor.

FIG. 19 shows graphs of the external quantum efficiency (EQE, left scale—black curve) and of the electroluminescence optical output power EL (right scale—gray curves) as a function of the gate-source voltage $V_{GS}$ while the drain contact was maintained at a constant bias voltage of −100V and the source contact was grounded ($V_{DS}$=−100V).

As shown in FIG. 19, the comparative device tested in this example showed much lower brightness (EL ~0.30 μW) compared to the device of Example 5 (EL ~2 μW). Further, the maximum brightness was obtained under conditions when the efficiency was not optimized, and vice versa (as indicated by the inverse relationships between the EQE and EL curves). Specifically, when EL was optimized to ~0.30 μW under the condition that $V_{GS}$=−100V, EQE was only ~0.15%. Conversely, when EQE was optimized to ~0.9% under the condition that $V_{GS}$=−20V, EL was only ~0.05 μW.

Table 2 below summarizes the materials used in each layer within the trilayer ambipolar channel of the OLET devices described in Examples 1-6, together with their respective maximum EL and EQE values.

TABLE 2

| Example | Trilayer ambipolar channel composition | | | Device Performance | |
|---|---|---|---|---|---|
| | 4 | 5 | 6 | EL$_{max}$ (μW) | EQE$_{max}$ (%) |
| 1 | C8-BTBT | TCTA/Ir(piq)$_3$ | N-F2-6 | ~45 | ~2.5* |
| 2 | C5-BTBT | TCTA/Ir(piq)$_3$ | N-F2-6 | >50 | >2.5 |
| 3 (comparative) | DNTT | TCTA/Ir(piq)$_3$ | N-F2-6 | ~20 | ~2.5 |
| 4 (comparative) | DFH4T (n-type) | Alq$_3$/DCM | DH4T (p-type) | <0.25 | ~0.8** |
| 5 | DH4T | TCTA/Ir(piq)$_3$ | N-F4-1 | 2 | >0.4 |
| 6 (comparative) | DH4T | Alq$_3$/PtOEP | N-F4-1 | 0.3 | <0.9*** |

*The maximum EL of ~45 μW was achieved when EQE was at a slightly reduced 2.25%.
**The maximum EL of <0.25 μW was achieved when EQE was <0.05% (when $V_{GS}$ = 60 V), while the maximum EQE of ~0.8% was achieved when EL was only ~0.025 (when $V_{GS}$ = 20 V).
***The maximum EL of 0.3 μW was achieved when EQE was ~0.5% (when $V_{GS}$ = −100 V), while the maximum EQE of ~0.9% was achieved when EL was <0.025 (when $V_{GS}$ = −20 V).

The invention claimed is:

1. An organic electroluminescent transistor comprising: at least one dielectric layer; at least one control electrode; at least one drain electrode; at least one source electrode; and an assembly comprising an emissive ambipolar channel, wherein:
said dielectric layer is arranged between said control electrode and said assembly;
said emissive ambipolar channel comprises at least one layer of an n-type semiconductor material, at least one layer of a p-type semiconductor material, and at least one layer of an emissive material arranged between said layers of p-type and n-type semiconductor materials, the emissive material including a fluorescent or phosphorescent emitter;
said p-type semiconductor material comprises a benzothieno-benzothiophene compound of formula (P-I)

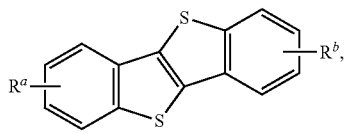
(P-I)

wherein $R^a$ and $R^b$ are independently selected from the group consisting of H, a $C_{1-18}$ alkyl group, and a $C_{6-14}$ aryl group;

said n-type semiconductor material comprises a bis(p-fluoroalkyl)phenyl-substituted oligomeric thiophene compound, wherein the oligomeric thiophene compound has 2, 3, 4, 5 or 6 thiophene moieties; and said emissive material comprises a blend material comprising an organic carbazole derivative as a host matrix compound and an iridium complex as a guest emitter.

2. The organic electroluminescent transistor according to claim 1, wherein said p-type semiconductor material comprises a benzothieno-benzothiophene compound of formula

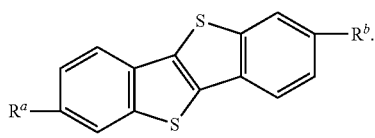

3. The organic electroluminescent transistor according to claim 1 where said p-type semiconductor material comprises a benzothieno-benzothiophene compound of formula

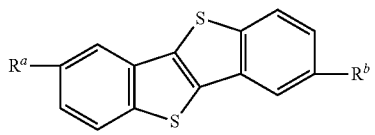

4. The organic electroluminescent transistor according to claim 2, wherein $R^a$ and $R^b$ are identical linear $C_{3-12}$ alkyl groups.

5. The organic electroluminescent transistor according to claim 1, wherein said p-type semiconductor material comprises a compound of the formula

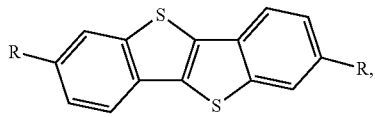

wherein each R is a phenyl group.

6. The organic electroluminescent transistor according to claim 1, wherein two or more of the thiophene moieties of the bis(p-fluoroalkyl)phenyl-substituted oligomeric thiophene compound are fused.

7. The organic electroluminescent transistor according to claim 6, wherein the bis(p-fluoroalkyl)phenyl-substituted oligomeric thiophene compound is a thienothiophene having the structural formula

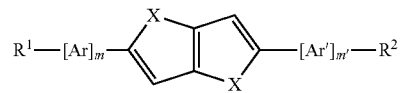

wherein Ar and Ar' are phenyl, m and m' are 1, and $R^1$ and $R^2$ are independently fluoroalkyl.

8. The organic electroluminescent transistor according to claim 1, wherein the thickness of said layer of p-type semiconductor material is between 5 and 50 nm.

9. The organic electroluminescent transistor according to claim 1, characterized in that the thickness of said layer of n-type semiconductor material is between 30 nm and 60 nm.

10. The organic electroluminescent transistor according to claim 9, wherein the thickness of said layer of p-type semiconductor material is between 15 and 45 nm.

11. The organic electroluminescent transistor according to claim 1, characterized in that said layer of emissive material has a thickness between 30 nm and 60 nm.

12. The organic electroluminescent transistor according to claim 1, wherein the organic carbazole derivative and the iridium complex are selected from the group consisting of:

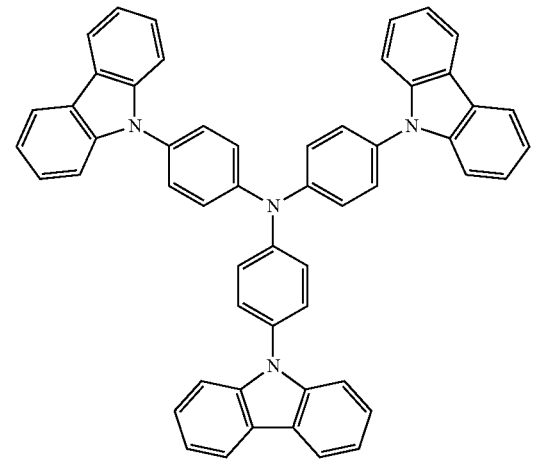
(H-1)

and

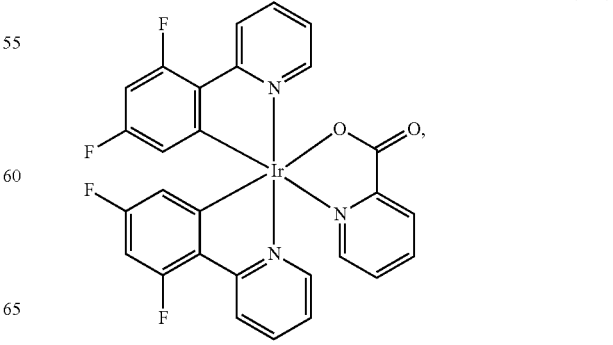
(G-1)

(H-2)
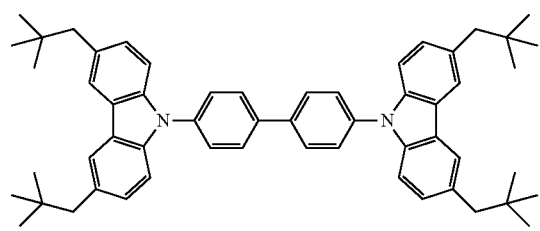
(H-1)
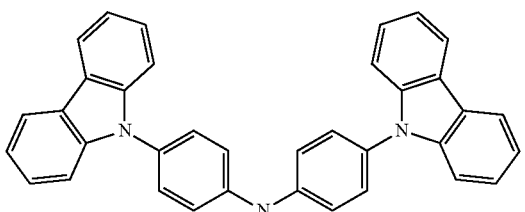
and
(G-1)
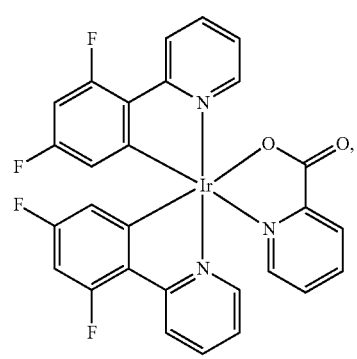
and
(H-3)
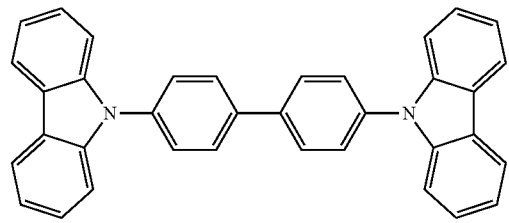
and
(G-2)
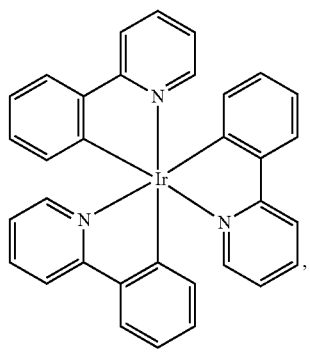
(H-2)
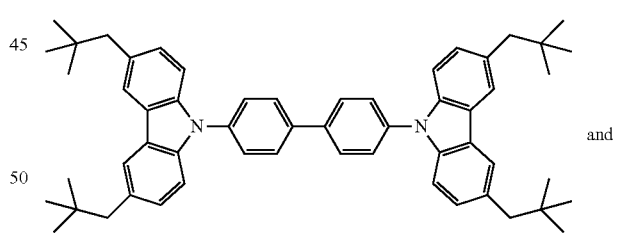
and
(G-1)
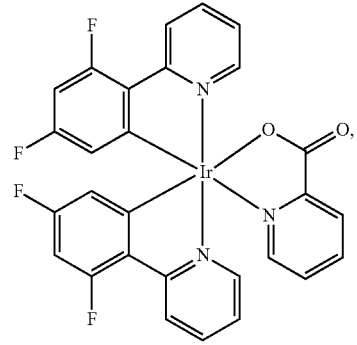
(G-2)
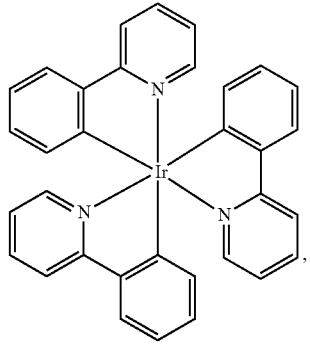

-continued (H-3)
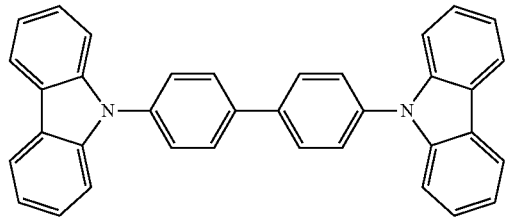
and (G-2)
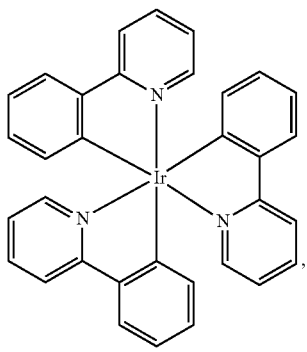, (H-2)
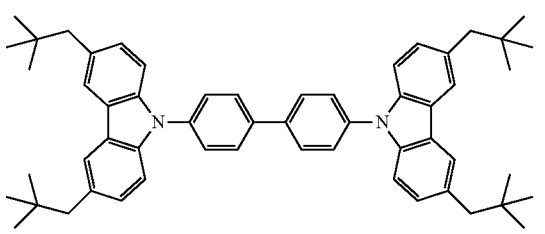
and (G-3)
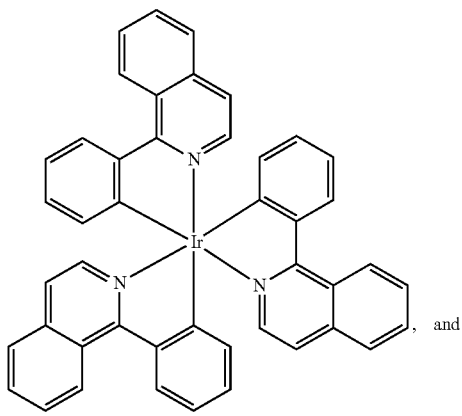, and (H-3)
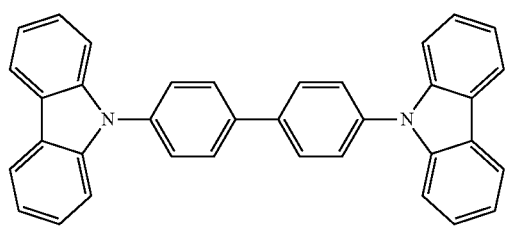
and -continued (G-3)
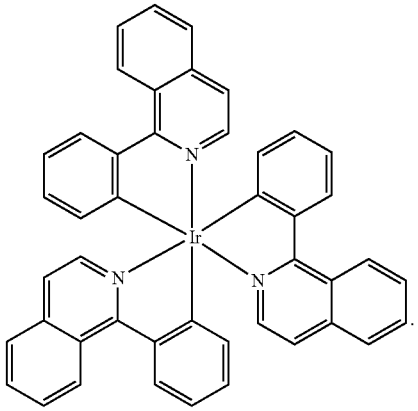.

13. The organic electroluminescent transistor according to claim 1, wherein said source electrode is in contact with said layer of p-type semiconductor material and said drain electrode is in contact with said layer of n-type semiconductor material.

14. The organic electroluminescent transistor according to claim 1, wherein said source electrode and said drain electrode are composed of at least one different material.

15. The organic electroluminescent transistor according to claim 1, wherein an injection sublayer is interposed between said source electrode and the layer of p-type or n-type semiconductor material and/or an injection sublayer is interposed between said drain electrode and the layer of the p-type or n-type semiconductor material.

16. The organic electroluminescent transistor according to claim 1, wherein each of the control electrode, drain electrode, and source electrode independently comprises a metal or a transparent conducting oxide selected from the group consisting of gold, silver, molybdenum, copper, titanium, chromium, tin-doped indium oxide and combination thereof.

17. The organic electroluminescent transistor according to claim 1, wherein the dielectric layer comprises an electrically insulating material selected from the group consisting of an inorganic oxide or nitride, a molecular dielectric, a polymeric dielectric, and combination thereof.

18. The organic electroluminescent transistor according to claim 17, wherein the inorganic oxide or nitride is selected from the group consisting of $SiO_2$, $Si_3N_4$, $Al_2O_3$, $ZrO_x$, Al-doped $ZrO_x$, and $HfO_x$.

19. The organic electroluminescent transistor according to claim 1, further comprising a passivation layer covering a top surface of the emissive ambipolar channel.

20. An optoelectronic device for producing an image, the optoelectronic device comprising a plurality of identical or different organic electroluminescent transistors according to claim 1, interconnected to each other and deposited on a substrate.

* * * * *